(12) United States Patent
Beraud et al.

(10) Patent No.: US 6,638,754 B1
(45) Date of Patent: Oct. 28, 2003

(54) MOTOR PROTEINS AND METHODS FOR THEIR USE

(75) Inventors: Christophe Beraud, San Francisco, CA (US); Roman Sakowicz, Foster City, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 6 days.

(21) Appl. No.: 10/112,432

(22) Filed: Mar. 29, 2002

Related U.S. Application Data

(63) Continuation of application No. 09/724,215, filed on Nov. 28, 2000, now abandoned.

(51) Int. Cl.[7] .......................... C12N 1/20; C12N 15/00; C12N 9/16; C12N 5/00; C12Q 1/68
(52) U.S. Cl. ................. 435/252.3; 435/196; 435/320.1; 435/6; 435/325; 536/232
(58) Field of Search ................. 536/23.2; 435/196, 435/252.3, 320.1, 325, 6

(56) References Cited

PUBLICATIONS

Wordeman et al., (1995) "Identification and partial characterization of mitotic centromere–associated kinesin, a kinesin–related protein that associates with centromeres during mitosis", J. Cell Bio. 128: 95–104.

Kim, et al., (1997) "Cloning and expression of human mitotic centromere–associated kinesin gene" Biochim, Biophys. Acta (1997) 1359:181–186.

U.S. patent application No. 09/314,464 Finer et al., Filed May 18, 1999, Title: Compositions and Assays Utilizing ADP or Phosphate for Detecting Protein Modulators.

Sequence alignment between Kim et al., 1997, (cited in the IDS) and sequences of this invention.

*Primary Examiner*—Maryam Monshipouri
(74) *Attorney, Agent, or Firm*—Lauren L. Stevens; Townsend and Townsend and Crew LLP

(57) ABSTRACT

The present invention provides high throughput screening systems for identifying compounds useful in the treatment of cellular proliferation disorders. The method can be performed in plurality simultaneously with fluorescence or absorbance readouts.

12 Claims, 17 Drawing Sheets

FIG. 1 atgggaggaaatcatgtcttgtgaaggaagtggaaaaaatgaagaacaagcgagaagagaagaaggcccagaactctgaaat
gagaatgaagagagctcaggagtatgacagtagttttccaaactgggaatttgcccgaatgattaaagaatttcgggctactttgg
aatgtcatccacttactatgactgatcctatcgaagagcacagaatatgtgtctgtgttaggaaacgcccactgaataagcaagaat
tggccaagaaagaaattgatgtgatttccattcctagcaagtgtctcctcttggtacatgaacccaagttgaaagtggacttaacaa
agtatctggagaaccaagcattctgctttgactttgcatttgatgaaacagcttcgaatgaagttgtctacaggttcacagcaaggc
cactggtacagacaatctttgaaggtggaaaagcaacttgttttgcatatggccagacaggaagtggcaagacacatactatggg
cggagacctctctgggaaagcccagaatgcatccaaagggatctatgccatggcctcccgggacgtcttcctcctgaagaatca
accctgctaccggaagttgggcctggaagtctatgtgacattcttcgagatctacaatgggaagctgtttgacctgctcaacaaga
aggccaagctgcgcgtgctggaggatggcaagcaacaggtgcaagtggtggggctgcaggagcatctggttaactctgctgat
gatgtcatcaagatgatcgacatgggcagcgcctgcagaacctctgggcagacatttgccaactccaattcctcccgctcccacg
cgtgcttccaaattattcttcgagctaaagggagaatgcatggcaagttctctttggtagatctggcagggaatgagcgaggcgc
ggacacttccagtgctgaccggcagacccgcatggagggcgcagaaatcaacaagagtctcttagccctgaaggagtgcatc
agggccctgggacagaacaaggctcacaccccgttccgtgagagcaagctgacacaggtgctgagggactccttcattgggg
agaactctaggacttgcatgattgccacgatctcaccaggcataagctcctgtgaatatactttaaacaccctgagatatgcagac
agggtcaaggagctgagcccccacagtgggcccagtggagagcagttgattcaaatggaaacagaagagatggaagcctgct
ctaacggggcgctgattccatga (SEQ ID NO:1)

FIG. 2 mrrksclvkevekmknkreekkaqnsemrmkraqeydssfpnwefarmikefratlechpltmtdpieehricvcvrkr
plnkqelakkeidvisipskclllvhepklkvdltkylenqafcfdfafdetasnevvyrftarplvqtifeggkatcfaygqtgs
gkthtmggdlsgkaqnaskgiyamasrdvfllknqpcyrklglevyvtfffeiyngklfdllnkkaklrvledgkqqvqvvgl
qehlvnsaddvikmidmgsacrtsgqtfansnssrshacfqiilrakgrmhgkfslvdlagnergadtssadrqtrmegaei
nksllalkeciralgqnkahtpfreskltqvlrdsfigensrtcmiatispgissceytlntlryadrvkelsphsgpsgeqliqme
teemeacsngalip*

(SEQ ID NO:2)

FIG. 3 atgcaaactgggaatttgcccgaatgattaaagaatttcgggctactttggaatgtcatccacttactatgactgatcctatcgaaga
gcacagaatatgtgtctgtgttaggaaacgcccactgaataagcaagaattggccaagaaagaaattgatgtgatttccattccta
gcaagtgtctcctcttggtacatgaacccaagttgaaagtggacttaacaaagtatctggagaaccaagcattctgctttgactttgc
atttgatgaaacagcttcgaatgaagttgtctacaggttcacagcaaggccactggtacagacaatctttgaaggtggaaaagca
acttgttttgcatatggccagacaggaagtggcaagacacatactatgggcggagacctctctgggaaagcccagaatgcatcc
aaagggatctatgccatggcctcccgggacgtcttcctcctgaagaatcaaccctgctaccggaagttgggcctggaagtctatg
tgacattcttcgagatctacaatgggaagctgtttgacctgctcaacaagaaggccaagctgcgcgtgctggaggatggcaagc
aacaggtgcaagtggtggggctgcaggagcatctggttaactctgctgatgatgtcatcaagatgatcgacatgggcagcgcct
gcagaacctctgggcagacatttgccaactccaattcctcccgctccacgcgtgcttccaaattattcttcgagctaaagggaga
atgcatggcaagttctctttggtagatctggcagggaatgagcgaggcgcggacacttccagtgctgaccggcagacccgcat
ggagggcgcagaaatcaacaagagtctcttagccctgaaggagtgcatcagggccctgggacagaacaaggctcacacccc
gttccgtgagagcaagctgacacaggtgctgagggactccttcattggggagaactctaggacttgcatgattgccacgatctca
ccaggcataagctcctgtgaatatactttaaacaccctgagatatgcagacagggtcaaggagctgagcccccacagtgggccc
agtggagagcagttgattcaaatggaaacagaagagatggaagcctgctctaacggggcgctgattccatga (SEQ ID NO:3)

FIG. 4 mpnwefarmikefratlechpltmtdpieehricvcvrkrplnkqelakkeidvisipskclllvhepklkvdltkylenqaf
cfdfafdetasnevvyrftarplvqtifeggkatcfaygqtgsgkthtmggdlsgkaqnaskgiyamasrdvfllknqpcyrk
lglevyvtffeiyngklfdllnkkaklrvledgkqqvqvvglqehlvnsaddvikmidmgsacrtsgqtfansnssrshacfq
iilrakgrmhgkfslvdlagnergadtssadrqtrmegaeinksllalkeciralgqnkahtpfreskltqvlrdsfigensrtcm
iatispgissceytlntlryadrvkelsphsgpsgeqliqmeteemeacsngalip*

(SEQ ID NO:4)

FIG. 5 atgacagaatatgtgtctgtgttaggaaacgcccactgaataagcaagaattggccaagaaagaaattgatgtgatttccattcta
gcaagtgtctcctcttggtacatgaacccaagttgaaagtggacttaacaaagtatctggagaaccaagcattctgctttgactttgc
atttgatgaaacagcttcgaatgaagttgtctacaggttcacagcaaggccactggtacagacaatctttgaaggtggaaaagca
acttgttttgcatatggccagacaggaagtggcaagacacatactatgggcggagacctctctgggaaagcccagaatgcatcc
aaagggatctatgccatggcctcccgggacgtcttcctcctgaagaatcaaccctgctaccggaagttgggcctggaagtctatg
tgacattcttcgagatctacaatgggaagctgtttgacctgctcaacaagaaggccaagctgcgcgtgctggaggatggcaagc
aacaggtgcaagtggtggggctgcaggagcatctggttaactctgctgatgatgtcatcaagatgatcgacatgggcagcgcct
gcagaacctctgggcagacatttgccaactccaattcctcccgctcccacgcgtgcttccaaattattcttcgagctaaagggaga
atgcatggcaagttctctttggtagatctggcagggaatgagcgaggcgcggacacttccagtgctgaccggcagacccgcat
ggagggcgcagaaatcaacaagagtctcttagccctgaaggagtgcatcagggccctgggacagaacaaggctcacacccc
gttccgtgagagcaagctgacacaggtgctgagggactccttcattggggagaactctaggacttgcatgattgccacgatctca
ccaggcataagctcctgtgaatatactttaaacaccctgagatatgcagacagggtcaaggagctgagcccccacagtgggccc
agtggagagcagttgattcaaatggaaacagaagagatggaagcctgctctaacggggcgctgattccatga (SEQ ID NO:5)

FIG. 6
Case 1042
Page 6 of 17 mhricvcvrkrplnkqelakkeidvisipskclllvhepklkvdltkylenqafcfdfafdetasnevvyrftarplvqtifegg
katcfaygqtgsgkthtmggdlsgkaqnaskgiyamasrdvfllknqpcyrklglevyvtffeiyngklfdllnkkaklrvle
dgkqqvqvvglqehlvnsaddvikmidmgsacrtsgqtfansnssrshacfqiilrakgrmhgkfslvdlagnergadtss
adrqtrmegaeinksllalkeciralgqnkahtpfreskltqvlrdsfigensrtcmiatispgissceytlntlryadrvkelsph
sgpsgeqliqmeteemeacsngalip*

(SEQ ID NO:6)

FIG. 7 atgggaggaaatcatgtcttgtgaaggaagtggaaaaaatgaagaacaagcgagaagagaagaaggcccagaactctgaaat
gagaatgaagagagctcaggagtatgacagtagttttccaaactggg aatttgcccgaatgattaaagaatttcgggctactttgg
aatgtcatccacttactatgactgatcctatcgaagagcacagaatatgtgtctgtgttaggaaacgcccactgaataagcaagaat
tggccaagaaagaaattgatgtgatttccattcctagcaagtgtctcctcttggtacatgaacccaagttgaaagtggacttaacaa
agtatctggagaaccaagcattctgctttgactttgcatttgatgaaacagcttcgaatgaagttgtctacaggttcacagcaaggc
cactggtacagacaatctttgaaggtggaaaagcaacttgttttgcatatggccagacaggaagtggaagacacatactatggg
cggagacctctctgggaaagcccagaatgcatccaaagggatctatgccatggcctcccgggacgtcttcctcctgaagaatca
accctgctaccggaagttgggcctggaagtctatgtgacattcttcgagatctacaatgggaagctgtttgacctgctcaacaaga
aggccaagctgcgcgtgctggaggatggcaagcaacaggtgcaagtggtggggctgcaggagcatctggttaactctgctgat
gatgtcatcaagatgatcgacatgggcagcgcctgcagaacctctggg cagacatttgccaactccaattcctcccgctcccacg
cgtgcttccaaattattcttcgagctaaagggagaatgcatggcaagttctctttggtagatctggcagggaatgagcgaggcgc
ggacacttccagtgctgaccggcagacccgcatggagggcgcagaaatcaacaagagtctcttagccctgaaggagtgcatc
agggccctgggacagaacaaggctcacaccccgttccgtgagagcaagctgacacaggtgctgagggactccttcattggggg
agaactctaggacttgcatgattgccacgatctcaccaggcataagctcctgtgaatatactttaaacaccctgagatatgcagac
agggtcaaggagctgagcccccacagtgggcccagtggagagcagttgattcaaatggaaacagaagagatggaagcctgct
ctaacggggcgctgattccaggcaatttatccaaggaagaggaggaactgtcttcccagatgtccagctttaacgaagccatgac
tcagatcagggagctggaggagaaggctatggaagagctcaaggagatcatacagcaaggaccatga (SEQ ID NO:7)

FIG. 8 mrrksclvkevekmknkreekkaqnsemrmkraqeydssfpnwefarmikefratlechpltmtdpieehricvcvrkr
plnkqelakkeidvisipskclllvhepklkvdltkylenqafcfdfafdetasnevvyrftarplvqtifeggkatcfaygqtgs
gkthtmggdlsgkaqnaskgiyamasrdvfllknqpcyrklglevyvtffeiyngklfdllnkkaklrvledgkqqvqvvgl
qehlvnsaddvikmidmgsacrtsgqtfansnssrshacfqiilrakgrnhgkfslvdlagnergadtssadrqtrmegaei
nksllalkeciralgqnkahtpfreskltqvlrdsfigensrtcmiatispgissceytlntlryadrvkelsphsgpsgeqliqme
teemeacsngalipgnlskeeeelssqmssfneamtqireleekameelkeiiqqgp*

(SEQ ID NO:8)

FIG. 9 atgcaaactgggaatttgcccgaatgattaaagaatttcgggctactttggaatgtcatccacttactatgactgatcctatcgaaga
gcacagaatatgtgtctgtgttaggaaacgcccactgaataagcaagaattggccaagaaagaaattgatgtgatttccattccta
gcaagtgtctcctcttggtacatgaacccaagttgaaagtggacttaacaaagtatctggagaaccaagcattctgctttgactttgc
atttgatgaaacagcttcgaatgaagttgtctacaggttcacagcaaggccactggtacagacaatctttgaaggtggaaaagca
acttgttttgcatatggccagacaggaagtggcaagacacatactatgggcggagacctctctgggaaagcccagaatgcatcc
aaagggatctatgccatggcctcccgggacgtcttcctcctgaagaatcaaccctgctaccggaagttgggcctggaagtctatg
tgacattcttcgagatctacaatgggaagctgtttgacctgctcaacaagaaggccaagctgcgcgtgctggaggatggcaagc
aacaggtgcaagtggtggggctgcaggagcatctggttaactctgctgatgatgtcatcaagatgatcgacatgggcagcgcct
gcagaacctctgggcagacatttgccaactccaattcctcccgctcccacgcgtgcttccaaattattcttcgagctaaagggaga
atgcatggcaagttctctttggtagatctggcagggaatgagcgaggcgcggacacttccagtgctgaccggcagaccgcat
ggagggcgcagaaatcaacaagagtctcttagccctgaaggagtgcatcagggccctgggacagaacaaggctcacacccc
gttccgtgagagcaagctgacacaggtgctgagggactccttcattggggagaactctaggacttgcatgattgccacgatctca
ccaggcataagctcctgtgaatatactttaaacaccctgagatatgcagacagggtcaaggagctgagccccacagtgggccc
agtggagagcagttgattcaaatggaaacagaagagatggaagcctgctctaacggggcgctgattccaggcaatttatccaag
gaagaggaggaactgtcttcccagatgtccagctttaacgaagccatgactcagatcagggagctggaggagaaggctatgga
agagctcaaggagatcatacagcaaggaccatga (SEQ ID NO:9)

FIG. 10 mpnwefarmikefratlechpltmtdpieehricvcvrkrplnkqelakkeidvisipskclllvhepklkvdltkylenqaf
cfdfafdetasnevvyrftarplvqtifeggkatcfaygqtgsgkthtmggdlsgkaqnaskgiyamasrdvfllknqpcyrk
lglevyvtffeiyngklfdllnkkaklrvledgkqqvqvvglqehlvnsaddvikmidmgsacrtsgqtfansnssrshacfq
iilrakgrmhgkfslvdlagnergadtssadrqtrmegaeirksllalkeciralgqnkahtpfreskltqvlrdsfigensrtcm
iatispgissceytlntlryadrvkelsphsgpsgeqliqmeteemeacsngalipgnlskeeeelssqmssfneamtqirele
ekameelkeiiqqgp*

(SEQ ID NO:10)

FIG. 11 atgacagaatatgtgtctgtgttaggaaacgcccactgaataagcaagaattggccaagaaagaaattgatgtgatttccattccta
gcaagtgtctcctcttggtacatgaacccaagttgaaagtggacttaacaaagtatctggagaaccaagcattctgctttgactttgc
atttgatgaaacagcttcgaatgaagttgtctacaggttcacagcaaggccactggtacagacaatctttgaaggtggaaaagca
acttgttttgcatatggccagacaggaagtggcaagacacatactatgggcggagacctctctgggaaagcccagaatgcatcc
aaagggatctatgccatggcctcccgggacgtcttcctcctgaagaatcaaccctgctaccggaagttgggcctggaagtctatg
tgacattcttcgagatctacaatgggaagctgtttgacctgctcaacaagaaggccaagctgcgcgtgctggaggatggcaagc
aacaggtgcaagtggtggggctgcaggagcatctggttaactctgctgatgatgtcatcaagatgatcgacatgggcagcgcct
gcagaacctctgggcagacatttgccaactccaattcctcccgctccacgcgtgcttccaaattattcttcgagctaaagggaga
atgcatggcaagttctctttggtagatctggcagggaatgagcgaggcgcggacacttccagtgctgaccggcagacccgcat
ggagggcgcagaaatcaacaagagtctcttagccctgaaggagtgcatcagggccctgggacagaacaaggctcacacccc
gttccgtgagagcaagctgacacaggtgctgagggactccttcattggggagaactctaggacttgcatgattgccacgatctca
ccaggcataagctcctgtgaatatactttaaacaccctgagatatgcagacagggtcaaggagctgagcccccacagtgggccc
agtggagagcagttgattcaaatggaaacagaagagatggaagcctgctctaacggggcgctgattccaggcaatttatccaag
gaagaggaggaactgtcttcccagatgtccagctttaacgaagccatgactcagatcagggagctggaggagaaggctatgga
agagctcaaggagatcatacagcaaggaccatga (SEQ ID NO:11)

FIG. 12 mhricvcvrkrplnkqelakkeidvisipskclllvhepklkvdltkylenqafcfdfafdetasnevvyrftarplvqtifegg
katcfaygqtgsgkthtmggdlsgkaqnaskgiyamasrdvfllknqpcyrklglevyvtffeiyngklfdllnkkaklrvle
dgkqqvqvvglqehlvnsaddvikmidmgsacrtsgqtfansnssrshacfqiilrakgrmhgkfslvdlagnergadtss
adrqtrmegaeinksllalkeciralgqnkahtpfreskltqvlrdsfigensrtcmiatispgissceytlntlryadrvkelsph
sgpsgeqliqmeteemeacsngalipgnlskeeeelssqmssfneamtqireleekameelkeiiqqgp[*]

(SEQ ID NO:12)

FIG. 13

```
atggactcgtcgcttcaggcccgcctgtttcccggtctcgctatcaagatccaacgcagtaatggtttaattcacagtgccaatgta
aggactgtgaacttggagaaatcctgtgtttcagtggaatgggcagaaggaggtgccacaaagggcaaagagattgattttgat
gatgtggctgcaataaacccagaactcttacagcttcttcccttacatccgaaggacaatctgcccttgcaggaaaatgtaacaatc
cagaaacaaaaacggagatccgtcaactccaaaattcctgctccaaaagaaagtcttcgaagccgctccactcgcatgtccact
gtctcagagcttcgcatcacggctcaggagaatgacatggaggtggagctgcctgcagctgcaaactcccgcaagcagttttca
gttcctcctgcccccactaggccttcctgccctgcagtggctgaaataccatgaggatggtcagcgaggagatggaagagcaa
gtccattccatccgtggcagctcttctgcaaaccctgtgaactcagttcggaggaaatcatgtcttgtgaaggaagtggaaaaaat
gaagaacaagcgagaagagaagaaggcccagaactctgaaatgagaatgaagagagctcaggagtatgacagtagttttcca
aactgggaatttgcccgaatgattaaagaatttcgggctactttggaatgtcatccacttactatgactgatcctatcgaagagcaca
gaatatgtgtctgtgttaggaaacgcccactgaataagcaagaattggccaagaaagaaattgatgtgatttccattcctagcaagt
gtctcctcttggtacatgaacccaagttgaaagtggacttaacaaagtatctggagaaccaagcattctgctttgactttgcatttgat
gaaacagcttcgaatgaagttgtctacaggttcacagcaaggccactggtacagacaatctttgaaggtggaaaagcaacttgttt
tgcatatggccagacaggaagtggcaagacacatactatgggcggagacctctctgggaaagcccagaatgcatccaaaggg
atctatgccatggcctcccgggacgtcttcctcctgaagaatcaaccctgctaccggaagttgggcctggaagtctatgtgacatt
cttcgagatctacaatgggaagctgtttgacctgctcaacaagaaggccaagctgcgcgtgctggaggatggcaagcaacagg
tgcaagtggtggggctgcaggagcatctggttaactctgctgatgatgtcatcaagatgatcgacatgggcagcgcctgcagaa
cctctgggcagacatttgccaactccaattcctcccgctcccacgcgtgcttccaaattattcttcgagctaaagggagaatgcatg
gcaagttctctttggtagatctggcagggaatgagcgaggcgcggacacttccagtgctgaccggcagacccgcatggaggg
cgcagaaatcaacaagagtctcttagccctgaaggagtgcatcagggccctgggacagaacaaggctcacaccccgttccgtg
agagcaagctgacacaggtgctgagggactccttcattggggagaactctaggacttgcatgattgccacgatctcaccaggca
taagctcctgtgaatatactttaaacaccctgagatatgcagacagggtcaaggagctgagcccccacagtgggcccagtggag
agcagttgattcaaatggaaacagaagagatggaagcctgctctaacggggcgctgattccaggcaatttatccaaggaagag
gaggaactgtcttcccagatgtccagctttaacgaagccatgactcagatcagggagctggaggagaaggctatggaagagct
caaggagatcatacagcaaggaccagactggcttgagctctctgagatgaccgagcagccagactatgacctggagacctttgt
gaacaaagcggaatctgctctggcccagcaagccaagcatttctcagccctgcgagatgtcatcaaggccttacgcctggccat
gcagctggaagagcaggctagcagacaaataagcagcaagaaacggccccagtga
```

(SEQ ID NO:13)

FIG. 14 mdsslqarlfpglaikiqrsnglihsanvrtvnlekscvsvewaeggatkgkeidfddvaainpellqllplhpkdnlplqen
vtiqkqkrrsvnskipapkeslrsrstrmstvselritaqendmevelpaaansrkqfsvppaptrpscpavaeiplrmvsee
meeqvhsirgsssanpvnsvrrksclvkevekmknkreekkaqnsemrrnkraqeydssfpnwefarmikefratlech
pltmtdpieehricvcvrkrplnkqelakkeidvisipskclllvhepklkvdltkylenqafcfdfafdetasnevvyrftarpl
vqtifeggkatcfaygqtgsgkthtmggdlsgkaqnaskgiyamasrdvfllknqpcyrklglevyvtffeiyngklfdllnk
kaklrvledgkqqvqvvglqehlvnsaddvikmidmgsacrtsgqtfansnssrshacfqiilrakgrmhgkfslvdlagn
ergadtssadrqtrmegaeinksllalkeciralgqnkahtpfreskltqvlrdsfigensrtcmiatispgissceytlntlryadr
vkelsphsgpsgeqliqmeteemeacsngalipgnlskeeelssqmssfneamtqireleekameelkeiiqqgpdwlel
semteqpdydletfvnkaesalaqqakhfsalrdvikalrlamqleeqasrqisskkrpq*

(SEQ ID NO:14)

FIG. 15A

```
gcgaaattga ggtttcttgg tattgcgcgt ttctcttcct tgctgactct ccgaatggcc
atggactcgt cgcttcaggc ccgcctgttt cccggtctcg ctatcaagat ccaacgcagt
aatggtttaa ttcacagtgc caatgtaagg actgtgaact tggagaaatc ctgtgtttca
gtggaatggg cagaaggagg tgccacaaag ggcaaagaga ttgattttga tgatgtggct
gcaataaacc cagaactctt acagcttctt cccttacatc cgaaggacaa tctgcccttg
caggaaaatg taacaatcca gaaacaaaaa cggagatccg tcaactccaa aattcctgct
ccaaaagaaa gtcttcgaag ccgctccact cgcatgtcca ctgtctcaga gcttcgcatc
acggctcagg agaatgacat ggaggtggag ctgcctgcag ctgcaaactc ccgcaagcag
ttttcagttc ctcctgcccc cactaggcct tcctgccctg cagtggctga ataccattg
aggatggtca gcgaggagat ggaagagcaa gtccattcca tccgtggcag ctcttctgca
aaccctgtga actcagttcg gaggaaatca tgtcttgtga aggaagtgga aaaaatgaag
aacaagcgag aagagaagaa ggcccagaac tctgaaatga gaatgaagag agctcaggag
tatgacagta gttttccaaa ctgggaattt gcccgaatga ttaaagaatt tcgggctact
ttggaatgtc atccacttac tatgactgat cctatcgaag agcacagaat atgtgtctgt
gttaggaaac gcccactgaa taagcaagaa ttggccaaga aagaaattga tgtgatttcc
attcctagca agtgtctcct cttggtacat gaacccaagt tgaaagtgga cttaacaaag
tatctggaga accaagcatt ctgctttgac tttgcatttg atgaaacagc ttcgaatgaa
gttgtctaca ggttcacagc aaggccactg gtacagacaa tctttgaagg tggaaaagca
acttgttttg catatggcca gacaggaagt ggcaagacac atactatggg cggagacctc
tctgggaaag cccagaatgc atccaaaggg atctatgcca tggcctcccg ggacgtcttc
ctcctgaaga atcaaccctg ctaccggaag ttgggcctgg aagtctatgt gacattcttc
gagatctaca atgggaagct gtttgacctg ctcaacaaga aggccaagct gcgcgtgctg
gaggacggca agcaacaggt gcaagtggtg gggctgcagg agcatctggt taactctgct
gatgatgtca tcaagatgct cgacatgggc agcgcctgca gaacctctgg cagacattt
gccaactcca attcctcccg ctcccacgcg tgcttccaaa ttattcttcg agctaaggg
```

FIG. 15B

```
agaatgcatg gcaagttctc tttggtagat ctggcaggga atgagcgagg cgcagacact
tccagtgctg accggcagac ccgcatggag ggcgcagaaa tcaacaagag tctcttagcc
ctgaaggagt gcatcagggc cctgggacag aacaaggctc acacccgtt ccgtgagagc
aagctgacac aggtgctgag ggactccttc attggggaga actctaggac ttgcatgatt
gccacgatct caccaggcat aagctcctgt gaatatactt taaacaccct gagatatgca
gacagggtca aggagctgag cccccacagt gggcccagtg gagagcagtt gattcaaatg
gaaacagaag agatggaagc ctgctctaac ggggcgctga ttccaggcaa tttatccaag
gaagaggagg aactgtcttc ccagatgtcc agctttaacg aagccatgac tcagatcagg
gagctggagg agaaggctat ggaagagctc aaggagatca tacagcaagg accagactgg
cttgagctct ctgagatgac cgagcagcca gactatgacc tggagacctt tgtgaacaaa
gcggaatctg ctctggccca gcaagccaag catttctcag ccctgcgaga tgtcatcaag
gccttacgcc tggccatgca gctggaagag caggctagca gacaaataag cagcaagaaa
cggccccagt gacgactgca aataaaaatc tgtttggttt gacacccagc ctcttccctg
gccctcccca gagaactttg ggtacctggt gggtctaggc agggtctgag ctgggacagg
ttctggtaaa tgccaagtat ggggcatct gggcccaggg cagctgggga gggggtcaga
gtgacatggg acactccttt tctgttcctc agttgtcgcc ctcacgagag gaaggagctc
ttagttaccc ttttgtgttg cccttctttc catcaagggg aatgttctca gcatagagct
ttctccgcag catcctgcct gcgtggactg gctgctaatg gagagctccc tggggttgtc
ctggctctgg ggagagagac ggagccttta gtacagctat ctgctggctc taaaccttct
acgcctttgg gccgagcact gaatgtcttg tactttaaaa aaatgtttct gagacctctt
tctactttac tgtctcccta gagtcctaga ggatccctac
```

(SEQ ID NO:15)

FIG. 16

MAMDSSLQARLFPGLAIKIQRSNGLIHSANVRTVNLEKSCVSVE

WAEGGATKGKEIDFDDVAAINPELLQLLPLHPKDNLPLQENVTIQKQKRRSVNSKIPA

PKESLRSRSTRMSTVSELRITAQENDMEVELPAAANSRKQFSVPPAPTRPSCPAVAEI

PLRMVSEEMEEQVHSIRGSSSANPVNSVRRKSCLVKEVEKMKNKREEKKAQNSEMRMK

RAQEYDSSFPNWEFARMIKEFRATLECHPLTMTDFIEEHRICVCVRKRPLNKQELAKK

EIDVISIPSKCLLLVHEPKLKVDLTKYLENQAFCFDFAFDETASNEVVYRFTARPLVQ

TIFEGGKATCFAYGQTGSGKTHTMGGDLSGKAQNASKGIYAMASRDVFLLKNQPCYEK

LGLEVYVTFFEIYNGKLFDLLNKKAKLRVLEDGKQQVQVVGLQEHLVNSADDVIKMLD

MGSACRTSGQTFANSNSSRSHACFQIILRAKGRMHGKFSLVDLAGNERGADTSSADRQ

TRMEGAEINKSLLALKECIRALGQNKAHTPFRESKLTQVLRDSFIGENSRTCMIATIS

PGISSCEYTLNTLRYADRVKELSPHSGPSGEQLIQMETEEMEACSNGALIPGNLSKEE

EELSSQMSSFNEAMTQIRELEEKAMEELKEIIQQGPDWLELSEMTEQPDYDLETFVNK

AESALAQQAKHFSALRDVIKALRLAMQLEEQASRQISSKKRPC (SEQ ID NO:16)

SEQUENCE LISTING

<160> NUMBER OF SEQ ID NOS: 16

<210> SEQ ID NO 1
<211> LENGTH: 1292
<212> TYPE: DNA
<213> ORGANISM: Human

<400> SEQUENCE: 1

| | | | | | |
|---|---|---|---|---|---|
| atgggaggaa | atcatgtctt | gtgaaggaag | tggaaaaaat | gaagaacaag | cgagaagaga | 60 |
| agaaggccca | gaactctgaa | atgagaatga | agagagctca | ggagtatgac | agtagttttc | 120 |
| caaactggga | atttgcccga | atgattaaag | aatttcgggc | tactttggaa | tgtcatccac | 180 |
| ttactatgac | tgatcctatc | gaagagcaca | gaatatgtgt | ctgtgttagg | aaacgcccac | 240 |
| tgaataagca | agaattggcc | aagaaagaaa | ttgatgtgat | ttccattcct | agcaagtgtc | 300 |
| tcctcttggt | acatgaaccc | aagttgaaag | tggacttaac | aaagtatctg | gagaaccaag | 360 |
| cattctgctt | tgactttgca | tttgatgaaa | cagcttcgaa | tgaagttgtc | tacaggttca | 420 |
| cagcaaggcc | actggtacag | acaatctttg | aaggtggaaa | agcaacttgt | tttgcatatg | 480 |
| gccagacagg | aagtggcaag | acacatacta | tgggcggaga | cctctctggg | aaagcccaga | 540 |
| atgcatccaa | agggatctat | gccatggcct | cccgggacgt | cttcctcctg | aagaatcaac | 600 |
| cctgctaccg | gaagttgggc | ctggaagtct | atgtgacatt | cttcgagatc | tacaatggga | 660 |
| agctgtttga | cctgctcaac | aagaaggcca | agctgcgcgt | gctggaggat | ggcaagcaac | 720 |
| aggtgcaagt | ggtggggctg | caggagcatc | tggttaactc | tgctgatgat | gtcatcaaga | 780 |
| tgatcgacat | gggcagcgcc | tgcagaacct | ctgggcagac | atttgccaac | tccaattcct | 840 |
| cccgctccca | cgcgtgcttc | caaattattc | ttcgagctaa | agggagaatg | catggcaagt | 900 |
| tctctttggt | agatctggca | gggaatgagc | gaggcgcgga | cacttccagt | gctgaccggc | 960 |
| agacccgcat | ggagggcgca | gaaatcaaca | agagtctctt | agccctgaag | gagtgcatca | 1020 |
| gggccctggg | acagaacaag | gctcacaccc | cgttccgtga | gagcaagctg | acacaggtgc | 1080 |
| tgagggactc | cttcattggg | gagaactcta | ggacttgcat | gattgccacg | atctcaccag | 1140 |
| gcataagctc | ctgtgaatat | actttaaaca | ccctgagata | tgcagacagg | gtcaaggagc | 1200 |
| tgagccccca | cagtgggccc | agtggagagc | agttgattca | aatggaaaca | gaagagatgg | 1260 |
| aagcctgctc | taacggggcg | ctgattccat | ga | | | 1292 |

<210> SEQ ID NO 2
<211> LENGTH: 430
<212> TYPE: PRT
<213> ORGANISM: Human

<400> SEQUENCE: 2

Met Arg Arg Lys Ser Cys Leu Val Lys Glu Val Lys Met Lys Asn
1               5                   10                  15

Lys Arg Glu Glu Lys Lys Ala Gln Asn Ser Glu Met Arg Met Lys Arg
                20                  25                  30

Ala Gln Glu Tyr Asp Ser Ser Phe Pro Asn Trp Glu Phe Ala Arg Met
            35                  40                  45

Ile Lys Glu Phe Arg Ala Thr Leu Glu Cys His Pro Leu Thr Met Thr
        50                  55                  60

Asp Pro Ile Glu Glu His Arg Ile Cys Val Cys Val Arg Lys Arg Pro
65                  70                  75                  80

```
Leu Asn Lys Gln Glu Leu Ala Lys Lys Glu Ile Asp Val Ile Ser Ile
                 85                  90                  95
Pro Ser Lys Cys Leu Leu Val His Glu Pro Lys Leu Lys Val Asp
            100                 105                 110
Leu Thr Lys Tyr Leu Glu Asn Gln Ala Phe Cys Phe Asp Phe Ala Phe
        115                 120                 125
Asp Glu Thr Ala Ser Asn Glu Val Val Tyr Arg Phe Thr Ala Arg Pro
    130                 135                 140
Leu Val Gln Thr Ile Phe Glu Gly Gly Lys Ala Thr Cys Phe Ala Tyr
145                 150                 155                 160
Gly Gln Thr Gly Ser Gly Lys Thr His Thr Met Gly Gly Asp Leu Ser
                165                 170                 175
Gly Lys Ala Gln Asn Ala Ser Lys Gly Ile Tyr Ala Met Ala Ser Arg
            180                 185                 190
Asp Val Phe Leu Leu Lys Asn Gln Pro Cys Tyr Arg Lys Leu Gly Leu
        195                 200                 205
Glu Val Tyr Val Thr Phe Phe Glu Ile Tyr Asn Gly Lys Leu Phe Asp
    210                 215                 220
Leu Leu Asn Lys Lys Ala Lys Leu Arg Val Leu Glu Asp Gly Lys Gln
225                 230                 235                 240
Gln Val Gln Val Val Gly Leu Gln Glu His Leu Val Asn Ser Ala Asp
                245                 250                 255
Asp Val Ile Lys Met Ile Asp Met Gly Ser Ala Cys Arg Thr Ser Gly
            260                 265                 270
Gln Thr Phe Ala Asn Ser Asn Ser Arg Ser His Ala Cys Phe Gln
        275                 280                 285
Ile Ile Leu Arg Ala Lys Gly Arg Met His Gly Lys Phe Ser Leu Val
    290                 295                 300
Asp Leu Ala Gly Asn Glu Arg Gly Ala Asp Thr Ser Ser Ala Asp Arg
305                 310                 315                 320
Gln Thr Arg Met Glu Gly Ala Glu Ile Asn Lys Ser Leu Leu Ala Leu
                325                 330                 335
Lys Glu Cys Ile Arg Ala Leu Gly Gln Asn Lys Ala His Thr Pro Phe
            340                 345                 350
Arg Glu Ser Lys Leu Thr Gln Val Leu Arg Asp Ser Phe Ile Gly Glu
        355                 360                 365
Asn Ser Arg Thr Cys Met Ile Ala Thr Ile Ser Pro Gly Ile Ser Ser
    370                 375                 380
Cys Glu Tyr Thr Leu Asn Thr Leu Arg Tyr Ala Asp Arg Val Lys Glu
385                 390                 395                 400
Leu Ser Pro His Ser Gly Pro Ser Gly Glu Gln Leu Ile Gln Met Glu
                405                 410                 415
Thr Glu Glu Met Glu Ala Cys Ser Asn Gly Ala Leu Ile Pro
            420                 425                 430

<210> SEQ ID NO 3
<211> LENGTH: 1175
<212> TYPE: DNA
<213> ORGANISM: Human

<400> SEQUENCE: 3
atgcaaactg ggaatttgcc cgaatgatta agaatttcg ggctactttg gaatgtcatc     60
cacttactat gactgatcct atcgaagagc acagaatatg tgtctgtgtt aggaaacgcc    120
cactgaataa gcaagaattg gccaagaaag aaattgatgt gatttccatt cctagcaagt    180
```

```
gtctcctctt ggtacatgaa cccaagttga aagtggactt aacaaagtat ctggagaacc    240
aagcattctg ctttgacttt gcatttgatg aaacagcttc gaatgaagtt gtctacaggt    300
tcacagcaag gccactggta cagacaatct ttgaaggtgg aaaagcaact tgttttgcat    360
atggccagac aggaagtggc aagacacata ctatgggcgg agacctctct gggaaagccc    420
agaatgcatc caaagggatc tatgccatgg cctcccggga cgtcttcctc ctgaagaatc    480
aaccctgcta ccggaagttg ggcctggaag tctatgtgac attcttcgag atctacaatg    540
ggaagctgtt tgacctgctc aacaagaagg ccaagctgcg cgtgctggag gatggcaagc    600
aacaggtgca agtggtgggg ctgcaggagc atctggttaa ctctgctgat gatgtcatca    660
agatgatcga catgggcagc gcctgcagaa cctctgggca gacatttgcc aactccaatt    720
cctcccgctc ccacgcgtgc ttccaaatta ttcttcgagc taagggagaa atgcatggca    780
agttctcttt ggtagatctg gcagggaatg agcgaggcgc ggacacttcc agtgctgacc    840
ggcagacccg catggagggc gcagaaatca acaagagtct cttagccctg aaggagtgca    900
tcagggccct gggacagaac aaggctcaca ccccgttccg tgagagcaag ctgacacagg    960
tgctgaggga ctccttcatt ggggagaact ctaggacttg catgattgcc acgatctcac   1020
caggcataag ctcctgtgaa tatactttaa acaccctgag atatgcagac agggtcaagg   1080
agctgagccc ccacagtggg cccagtggag agcagttgat tcaaatggaa acagaagaga   1140
tggaagcctg ctctaacggg gcgctgattc catga                              1175
```

<210> SEQ ID NO 4
<211> LENGTH: 391
<212> TYPE: PRT
<213> ORGANISM: Protein

<400> SEQUENCE: 4

```
Met Pro Asn Trp Glu Phe Ala Arg Met Ile Lys Glu Phe Arg Ala Thr
 1               5                  10                  15

Leu Glu Cys His Pro Leu Thr Met Thr Asp Pro Ile Glu Glu His Arg
            20                  25                  30

Ile Cys Val Cys Val Arg Lys Arg Pro Leu Asn Lys Gln Glu Leu Ala
        35                  40                  45

Lys Lys Glu Ile Asp Val Ile Ser Ile Pro Ser Lys Cys Leu Leu Leu
    50                  55                  60

Val His Glu Pro Lys Leu Lys Val Asp Leu Thr Lys Tyr Leu Glu Asn
65                  70                  75                  80

Gln Ala Phe Cys Phe Asp Phe Ala Phe Asp Glu Thr Ala Ser Asn Glu
                85                  90                  95

Val Val Tyr Arg Phe Thr Ala Arg Pro Leu Val Gln Thr Ile Phe Glu
            100                 105                 110

Gly Gly Lys Ala Thr Cys Phe Ala Tyr Gly Gln Thr Gly Ser Gly Lys
        115                 120                 125

Thr His Thr Met Gly Gly Asp Leu Ser Gly Lys Ala Gln Asn Ala Ser
    130                 135                 140

Lys Gly Ile Tyr Ala Met Ala Ser Arg Asp Val Phe Leu Leu Lys Asn
145                 150                 155                 160

Gln Pro Cys Tyr Arg Lys Leu Gly Leu Glu Val Tyr Val Thr Phe Phe
                165                 170                 175

Glu Ile Tyr Asn Gly Lys Leu Phe Asp Leu Leu Asn Lys Lys Ala Lys
            180                 185                 190
```

```
Leu Arg Val Leu Glu Asp Gly Lys Gln Gln Val Gln Val Val Gly Leu
            195                 200                 205

Gln Glu His Leu Val Asn Ser Ala Asp Asp Val Ile Lys Met Ile Asp
            210                 215                 220

Met Gly Ser Ala Cys Arg Thr Ser Gly Gln Thr Phe Ala Asn Ser Asn
225                 230                 235                 240

Ser Ser Arg Ser His Ala Cys Phe Gln Ile Ile Leu Arg Ala Lys Gly
            245                 250                 255

Arg Met His Gly Lys Phe Ser Leu Val Asp Leu Ala Gly Asn Glu Arg
            260                 265                 270

Gly Ala Asp Thr Ser Ser Ala Asp Arg Gln Thr Arg Met Glu Gly Ala
            275                 280                 285

Glu Ile Asn Lys Ser Leu Leu Ala Leu Lys Glu Cys Ile Arg Ala Leu
            290                 295                 300

Gly Gln Asn Lys Ala His Thr Pro Phe Arg Glu Ser Lys Leu Thr Gln
305                 310                 315                 320

Val Leu Arg Asp Ser Phe Ile Gly Glu Asn Ser Arg Thr Cys Met Ile
            325                 330                 335

Ala Thr Ile Ser Pro Gly Ile Ser Ser Cys Glu Tyr Thr Leu Asn Thr
            340                 345                 350

Leu Arg Tyr Ala Asp Arg Val Lys Glu Leu Ser Pro His Ser Gly Pro
            355                 360                 365

Ser Gly Glu Gln Leu Ile Gln Met Glu Thr Glu Met Glu Ala Cys
370                 375                 380

Ser Asn Gly Ala Leu Ile Pro
385                 390

<210> SEQ ID NO 5
<211> LENGTH: 1088
<212> TYPE: DNA
<213> ORGANISM: Human

<400> SEQUENCE: 5
atgacagaat atgtgtctgt gttaggaaac gcccactgaa taagcaagaa ttggccaaga      60
aagaaattga tgtgatttcc attcctagca agtgtctcct cttggtacat gaacccaagt    120
tgaaagtgga cttaacaaag tatctggaga accaagcatt ctgctttgac tttgcatttg    180
atgaaacagc ttcgaatgaa gttgtctaca ggttcacagc aaggccactg gtacagacaa    240
tctttgaagg tggaaaagca acttgttttg catatgccga acaggaagt ggcaagacac    300 atactatggg cggagacctc tctgggaaag cccagaatgc atccaaaggg atctatgcca    360
tggcctcccg ggacgtcttc ctcctgaaga atcaaccctg ctaccggaag ttgggcctgg    420
aagtctatgt gacattcttc gagatctaca tgggaagct gtttgacctg ctcaacaaga    480
aggccaagct gcgcgtgctg gaggatggca agcaacaggg gcaagtggtg gggctgcagg    540
agcatctggt taactctgct gatgatgtca tcaagatgat cgacatgggc agcgcctgca    600
gaacctctgg gcagacattt gccaactcca attcctcccg ctcccacgcg tgcttccaaa    660
ttattcttcg agctaaaggg agaatgcatg gcaagttctc tttggtagat ctggcaggga    720
atgagcgagg cgcggacact tccagtgctg accggcagac ccgcatggag ggcgcagaaa    780
tcaacaagag tctcttagcc ctgaaggagt gcatcagggc cctgggacag aacaaggctc    840
acaccccgtt ccgtgagagc aagctgacac aggtgctgag ggactccttc attggggaga    900
actctaggac ttgcatgatt gccacgatct caccaggcat aagctcctgt gaatatactt    960
```

-continued

```
taaacaccct gagatatgca gacagggtca aggagctgag cccccacagt gggcccagtg    1020
gagagcagtt gattcaaatg gaaacagaag agatggaagc tgctctaac ggggcgctga    1080 ttccatga                                                             1088
```

<210> SEQ ID NO 6
<211> LENGTH: 362
<212> TYPE: PRT
<213> ORGANISM: Human

<400> SEQUENCE: 6

```
Met His Arg Ile Cys Val Cys Val Arg Lys Arg Pro Leu Asn Lys Gln
 1               5                  10                  15

Glu Leu Ala Lys Lys Glu Ile Asp Val Ile Ser Ile Pro Ser Lys Cys
             20                  25                  30

Leu Leu Leu Val His Glu Pro Lys Leu Lys Val Asp Leu Thr Lys Tyr
         35                  40                  45

Leu Glu Asn Gln Ala Phe Cys Phe Asp Phe Ala Phe Asp Glu Thr Ala
     50                  55                  60

Ser Asn Glu Val Val Tyr Arg Phe Thr Ala Arg Pro Leu Val Gln Thr
 65                  70                  75                  80

Ile Phe Glu Gly Gly Lys Ala Thr Cys Phe Ala Tyr Gly Gln Thr Gly
                 85                  90                  95

Ser Gly Lys Thr His Thr Met Gly Gly Asp Leu Ser Gly Lys Ala Gln
            100                 105                 110

Asn Ala Ser Lys Gly Ile Tyr Ala Met Ala Ser Arg Asp Val Phe Leu
        115                 120                 125

Leu Lys Asn Gln Pro Cys Tyr Arg Lys Leu Gly Leu Glu Val Tyr Val
    130                 135                 140

Thr Phe Phe Glu Ile Tyr Asn Gly Lys Leu Phe Asp Leu Leu Asn Lys
145                 150                 155                 160

Lys Ala Lys Leu Arg Val Leu Glu Asp Gly Lys Gln Gln Val Gln Val
                165                 170                 175

Val Gly Leu Gln Glu His Leu Val Asn Ser Ala Asp Val Ile Lys
            180                 185                 190

Met Ile Asp Met Gly Ser Ala Cys Arg Thr Ser Gly Gln Thr Phe Ala
        195                 200                 205

Asn Ser Asn Ser Ser Arg Ser His Ala Cys Phe Gln Ile Ile Leu Arg
    210                 215                 220

Ala Lys Gly Arg Met His Gly Lys Phe Ser Leu Val Asp Leu Ala Gly
225                 230                 235                 240

Asn Glu Arg Gly Ala Asp Thr Ser Ser Ala Asp Arg Gln Thr Arg Met
                245                 250                 255

Glu Gly Ala Glu Ile Asn Lys Ser Leu Leu Ala Leu Lys Glu Cys Ile
            260                 265                 270

Arg Ala Leu Gly Gln Asn Lys Ala His Thr Pro Phe Arg Glu Ser Lys
        275                 280                 285

Leu Thr Gln Val Leu Arg Asp Ser Phe Ile Gly Glu Asn Ser Arg Thr
    290                 295                 300

Cys Met Ile Ala Thr Ile Ser Pro Gly Ile Ser Ser Cys Glu Tyr Thr
305                 310                 315                 320

Leu Asn Thr Leu Arg Tyr Ala Asp Arg Val Lys Glu Leu Ser Pro His
                325                 330                 335

Ser Gly Pro Ser Gly Glu Gln Leu Ile Gln Met Glu Thr Glu Glu Met
            340                 345                 350
```

Glu Ala Cys Ser Asn Gly Ala Leu Ile Pro
        355                 360

<210> SEQ ID NO 7
<211> LENGTH: 1421
<212> TYPE: DNA
<213> ORGANISM: Human

<400> SEQUENCE: 7

| | | | | | |
|---|---|---|---|---|---|
| atgggaggaa | atcatgtctt | gtgaaggaag | tggaaaaaat | gaagaacaag cgagaagaga | 60 |
| agaaggccca | gaactctgaa | atgagaatga | agagagctca | ggagtatgac agtagttttc | 120 |
| caaactggga | atttgcccga | atgattaaag | aatttcgggc | tactttggaa tgtcatccac | 180 |
| ttactatgac | tgatcctatc | gaagagcaca | gaatatgtgt | ctgtgttagg aaacgcccac | 240 |
| tgaataagca | agaattggcc | aagaaagaaa | ttgatgtgat | ttccattcct agcaagtgtc | 300 |
| tcctcttggt | acatgaaccc | aagttgaaag | tggacttaac | aaagtatctg agaaccaag | 360 |
| cattctgctt | tgactttgca | tttgatgaaa | cagcttcgaa | tgaagttgtc tacaggttca | 420 |
| cagcaaggcc | actggtacag | acaatctttg | aaggtggaaa | agcaacttgt tttgcatatg | 480 |
| gccagacagg | aagtggcaag | acacatacta | tgggcggaga | cctctctggg aaagcccaga | 540 |
| atgcatccaa | aggatctat | gccatggcct | cccgggacgt | cttcctcctg aagaatcaac | 600 |
| cctgctaccg | gaagttgggc | ctggaagtct | atgtgacatt | cttcgagatc tacaatggga | 660 |
| agctgtttga | cctgctcaac | aagaaggcca | agctgcgcgt | gctggaggat ggcaagcaac | 720 |
| aggtgcaagt | ggtggggctg | caggagcatc | tggttaactc | tgctgatgat gtcatcaaga | 780 |
| tgatcgacat | gggcagcgcc | tgcagaacct | ctgggcagac | atttgccaac tccaattcct | 840 |
| cccgctccca | cgcgtgcttc | caaattattc | ttcgagctaa | agggagaatg catggcaagt | 900 |
| tctctttggt | agatctggca | gggaatgagc | gaggcgcgga | cacttccagt gctgaccggc | 960 |
| agacccgcat | ggagggcgca | gaaatcaaca | agagtctctt | agccctgaag gagtgcatca | 1020 |
| gggccctggg | acagaacaag | gctcacaccc | cgttccgtga | gagcaagctg acacaggtgc | 1080 |
| tgagggactc | cttcattggg | gagaactcta | ggacttgcat | gattgccacg atctcaccag | 1140 |
| gcataagctc | ctgtgaatat | actttaaaca | ccctgagata | tgcagacagg gtcaaggagc | 1200 |
| tgagccccca | cagtgggccc | agtggagagc | agttgattca | aatggaaaca gaagagatgg | 1260 |
| aagcctgctc | taacggggcg | ctgattccag | gcaatttatc | caaggaagag gaggaactgt | 1320 |
| cttcccagat | gtccagctttt | aacgaagcca | tgactcagat | cagggagctg gaggagaagg | 1380 |
| ctatggaaga | gctcaaggag | atcatacagc | aaggaccatg | a | 1421 |

<210> SEQ ID NO 8
<211> LENGTH: 473
<212> TYPE: PRT
<213> ORGANISM: Human

<400> SEQUENCE: 8

Met Arg Arg Lys Ser Cys Leu Val Lys Glu Val Glu Lys Met Lys Asn
 1               5                  10                  15

Lys Arg Glu Glu Lys Lys Ala Gln Asn Ser Glu Met Arg Met Lys Arg
            20                  25                  30

Ala Gln Glu Tyr Asp Ser Ser Phe Pro Asn Trp Glu Phe Ala Arg Met
        35                  40                  45

Ile Lys Glu Phe Arg Ala Thr Leu Glu Cys His Pro Leu Thr Met Thr
    50                  55                  60

```
Asp Pro Ile Glu Glu His Arg Ile Cys Val Cys Val Arg Lys Arg Pro
 65                  70                  75                  80

Leu Asn Lys Gln Glu Leu Ala Lys Lys Glu Ile Asp Val Ile Ser Ile
                 85                  90                  95

Pro Ser Lys Cys Leu Leu Val His Glu Pro Lys Leu Lys Val Asp
                100                 105                 110

Leu Thr Lys Tyr Leu Glu Asn Gln Ala Phe Cys Phe Asp Phe Ala Phe
                115                 120                 125

Asp Glu Thr Ala Ser Asn Glu Val Val Tyr Arg Phe Thr Ala Arg Pro
130                 135                 140

Leu Val Gln Thr Ile Phe Glu Gly Lys Ala Thr Cys Phe Ala Tyr
145                 150                 155                 160

Gly Gln Thr Gly Ser Gly Lys Thr His Thr Met Gly Gly Asp Leu Ser
                165                 170                 175

Gly Lys Ala Gln Asn Ala Ser Lys Gly Ile Tyr Ala Met Ala Ser Arg
                180                 185                 190

Asp Val Phe Leu Leu Lys Asn Gln Pro Cys Tyr Arg Lys Leu Gly Leu
                195                 200                 205

Glu Val Tyr Val Thr Phe Phe Glu Ile Tyr Asn Gly Lys Leu Phe Asp
                210                 215                 220

Leu Leu Asn Lys Lys Ala Lys Leu Arg Val Leu Glu Asp Gly Lys Gln
225                 230                 235                 240

Gln Val Gln Val Val Gly Leu Gln Glu His Leu Val Asn Ser Ala Asp
                245                 250                 255

Asp Val Ile Lys Met Ile Asp Met Gly Ser Ala Cys Arg Thr Ser Gly
                260                 265                 270

Gln Thr Phe Ala Asn Ser Asn Ser Ser Arg Ser His Ala Cys Phe Gln
                275                 280                 285

Ile Ile Leu Arg Ala Lys Gly Arg Met His Gly Lys Phe Ser Leu Val
                290                 295                 300

Asp Leu Ala Gly Asn Glu Arg Gly Ala Asp Thr Ser Ser Ala Asp Arg
305                 310                 315                 320

Gln Thr Arg Met Glu Gly Ala Glu Ile Asn Lys Ser Leu Leu Ala Leu
                325                 330                 335

Lys Glu Cys Ile Arg Ala Leu Gly Gln Asn Lys Ala His Thr Pro Phe
                340                 345                 350

Arg Glu Ser Lys Leu Thr Gln Val Leu Arg Asp Ser Phe Ile Gly Glu
                355                 360                 365

Asn Ser Arg Thr Cys Met Ile Ala Thr Ile Ser Pro Gly Ile Ser Ser
                370                 375                 380

Cys Glu Tyr Thr Leu Asn Thr Leu Arg Tyr Ala Asp Arg Val Lys Glu
385                 390                 395                 400

Leu Ser Pro His Ser Gly Pro Ser Gly Glu Gln Leu Ile Gln Met Glu
                405                 410                 415

Thr Glu Glu Met Glu Ala Cys Ser Asn Gly Ala Leu Ile Pro Gly Asn
                420                 425                 430

Leu Ser Lys Glu Glu Glu Leu Ser Ser Gln Met Ser Ser Phe Asn
                435                 440                 445

Glu Ala Met Thr Gln Ile Arg Glu Leu Glu Glu Lys Ala Met Glu Glu
                450                 455                 460

Leu Lys Glu Ile Ile Gln Gln Gly Pro
465                 470
```

-continued

```
<210> SEQ ID NO 9
<211> LENGTH: 1304
<212> TYPE: DNA
<213> ORGANISM: Human

<400> SEQUENCE: 9
atgcaaactg ggaatttgcc cgaatgatta agaatttcg ggctactttg gaatgtcatc      60
cacttactat gactgatcct atcgaagagc acagaatatg tgtctgtgtt aggaaacgcc     120
cactgaataa gcaagaattg ccaagaaaag aaattgatgt gatttccatt cctagcaagt    180
gtctcctctt ggtacatgaa cccaagttga agtggactt aacaaagtat ctggagaacc     240
aagcattctg ctttgacttt gcatttgatg aaacagcttc gaatgaagtt gtctacaggt    300
tcacagcaag gccactggta cagacaatct ttgaaggtgg aaaagcaact tgttttgcat    360
atggccagac aggaagtggc aagacacata ctatgggcgg agacctctct gggaaagccc    420
agaatgcatc caaagggatc tatgccatgg cctcccggga cgtcttcctc ctgaagaatc    480
aaccctgcta ccggaagttg gcctggaag tctatgtgac attcttcgag atctacaatg    540
ggaagctgtt tgacctgctc aacaagaagg ccaagctgcg cgtgctggag gatggcaagc    600
aacaggtgca agtggtgggg ctgcaggagc atctggttaa ctctgctgat gatgtcatca    660
agatgatcga catgggcagc gcctgcagaa cctctgggca gacatttgcc aactccaatt    720
cctcccgctc ccacgcgtgc ttccaaatta ttcttcgagc taaagggaga atgcatggca    780
agttctcttt ggtagatctg gcagggatg agcgaggcgc ggacacttcc agtgctgacc    840
ggcagacccg catggagggc gcagaaatca acaagagtct cttagccctg aaggagtgca    900
tcagggccct gggacagaac aaggctcaca ccccgttccg tgagagcaag ctgacacagg    960
tgctgaggga ctccttcatt ggggagaact ctaggacttg catgattgcc acgatctcac    1020
caggcataag ctcctgtgaa tatactttaa acaccctgag atatgcagac agggtcaagg   1080
agctgagccc ccacagtggg cccagtggag agcagttgat tcaaatggaa acagaagaga   1140
tggaagcctg ctctaacggg gcgctgattc aggcaatttt atccaaggaa gaggaggaac   1200
tgtcttccca gatgtccagc tttaacgaag ccatgactca gatcagggag ctggaggaga   1260
aggctatgga agagctcaag gagatcatac agcaaggacc atga                   1304

<210> SEQ ID NO 10
<211> LENGTH: 434
<212> TYPE: PRT
<213> ORGANISM: Human

<400> SEQUENCE: 10

Met Pro Asn Trp Glu Phe Ala Arg Met Ile Lys Glu Phe Arg Ala Thr
 1               5                  10                  15

Leu Glu Cys His Pro Leu Thr Met Thr Asp Pro Ile Glu Glu His Arg
            20                  25                  30

Ile Cys Val Cys Val Arg Lys Arg Pro Leu Asn Lys Gln Glu Leu Ala
        35                  40                  45

Lys Lys Glu Ile Asp Val Ile Ser Ile Pro Ser Lys Cys Leu Leu Leu
    50                  55                  60

Val His Glu Pro Lys Leu Lys Val Asp Leu Thr Lys Tyr Leu Glu Asn
65                  70                  75                  80

Gln Ala Phe Cys Phe Asp Phe Ala Phe Asp Glu Thr Ala Ser Asn Glu
                85                  90                  95

Val Val Tyr Arg Phe Thr Ala Arg Pro Leu Val Gln Thr Ile Phe Glu
```

```
                    100                 105                 110
Gly Gly Lys Ala Thr Cys Phe Ala Tyr Gly Gln Thr Gly Ser Gly Lys
            115                 120                 125

Thr His Thr Met Gly Gly Asp Leu Ser Gly Lys Ala Gln Asn Ala Ser
    130                 135                 140

Lys Gly Ile Tyr Ala Met Ala Ser Arg Asp Val Phe Leu Leu Lys Asn
145                 150                 155                 160

Gln Pro Cys Tyr Arg Lys Leu Gly Leu Glu Val Tyr Val Thr Phe Phe
                165                 170                 175

Glu Ile Tyr Asn Gly Lys Leu Phe Asp Leu Leu Asn Lys Lys Ala Lys
            180                 185                 190

Leu Arg Val Leu Glu Asp Gly Lys Gln Gln Val Gln Val Val Gly Leu
        195                 200                 205

Gln Glu His Leu Val Asn Ser Ala Asp Asp Val Ile Lys Met Ile Asp
    210                 215                 220

Met Gly Ser Ala Cys Arg Thr Ser Gly Gln Thr Phe Ala Asn Ser Asn
225                 230                 235                 240

Ser Ser Arg Ser His Ala Cys Phe Gln Ile Ile Leu Arg Ala Lys Gly
                245                 250                 255

Arg Met His Gly Lys Phe Ser Leu Val Asp Leu Ala Gly Asn Glu Arg
            260                 265                 270

Gly Ala Asp Thr Ser Ser Ala Asp Arg Gln Thr Arg Met Glu Gly Ala
        275                 280                 285

Glu Ile Asn Lys Ser Leu Leu Ala Leu Lys Glu Cys Ile Arg Ala Leu
    290                 295                 300

Gly Gln Asn Lys Ala His Thr Pro Phe Arg Glu Ser Lys Leu Thr Gln
305                 310                 315                 320

Val Leu Arg Asp Ser Phe Ile Gly Glu Asn Ser Arg Thr Cys Met Ile
                325                 330                 335

Ala Thr Ile Ser Pro Gly Ile Ser Ser Cys Glu Tyr Thr Leu Asn Thr
            340                 345                 350

Leu Arg Tyr Ala Asp Arg Val Lys Glu Leu Ser Pro His Ser Gly Pro
        355                 360                 365

Ser Gly Glu Gln Leu Ile Gln Met Glu Thr Glu Glu Met Glu Ala Cys
    370                 375                 380

Ser Asn Gly Ala Leu Ile Pro Gly Asn Leu Ser Lys Glu Glu Glu Glu
385                 390                 395                 400

Leu Ser Ser Gln Met Ser Ser Phe Asn Glu Ala Met Thr Gln Ile Arg
                405                 410                 415

Glu Leu Glu Glu Lys Ala Met Glu Glu Leu Lys Glu Ile Ile Gln Gln
            420                 425                 430

Gly Pro

<210> SEQ ID NO 11
<211> LENGTH: 1217
<212> TYPE: DNA
<213> ORGANISM: Human

<400> SEQUENCE: 11
atgacagaat atgtgtctgt gttaggaaac gcccactgaa taagcaagaa ttggccaaga    60
aagaaattga tgtgatttcc attcctagca agtgtctcct cttggtacat gaacccaagt   120
tgaaagtgga cttaacaaag tatctggaga ccaagcatt  ctgctttgac tttgcatttg   180
atgaaacagc ttcgaatgaa gttgtctaca ggttcacagc aaggccactg gtacagacaa   240
```

-continued

```
tctttgaagg tggaaaagca acttgttttg catatggcca gacaggaagt ggcaagacac    300
atactatggg cggagacctc tctgggaaag cccagaatgc atccaaaggg atctatgcca    360
tggcctcccg ggacgtcttc ctcctgaaga atcaaccctg ctaccggaag ttgggcctgg    420
aagtctatgt gacattcttc gagatctaca atgggaagct gtttgacctg ctcaacaaga    480
aggccaagct gcgcgtgctg gaggatggca agcaacaggt gcaagtggtg gggctgcagg    540
agcatctggt taactctgct gatgatgtca tcaagatgat cgacatgggc agcgcctgca    600
gaacctctgg gcagacattt gccaactcca attcctcccg ctcccacgcg tgcttccaaa    660
ttattcttcg agctaaaggg agaatgcatg gcaagttctc tttggtagat ctggcaggga    720
atgagcgagg cgcggacact tccagtgctg accggcagac ccgcatggag ggcgcagaaa    780
tcaacaagag tctcttagcc ctgaaggagt gcatcagggc cctgggacag aacaaggctc    840
acaccccgtt ccgtgagagc aagctgacac aggtgctgag ggactccttc attggggaga    900
actctaggac ttgcatgatt gccacgatct caccaggcat aagctcctgt gaatatactt    960
taaacaccct gagatatgca gacagggtca aggagctgag cccccacagt gggcccagtg   1020
gagagcagtt gattcaaatg gaaacagaag agatggaagc ctgctctaac ggggcgctga   1080
ttccaggcaa tttatccaag gaagaggagg aactgtcttc ccagatgtcc agctttaacg   1140
aagccatgac tcagatcagg gagctggagg agaaggctat ggaagagctc aaggagatca   1200
tacagcaagg accatga                                                  1217
```

<210> SEQ ID NO 12
<211> LENGTH: 405
<212> TYPE: PRT
<213> ORGANISM: Human

<400> SEQUENCE: 12

```
Met His Arg Ile Cys Val Cys Val Arg Lys Arg Pro Leu Asn Lys Gln
  1               5                  10                  15
Glu Leu Ala Lys Lys Glu Ile Asp Val Ile Ser Ile Pro Ser Lys Cys
             20                  25                  30
Leu Leu Leu Val His Glu Pro Lys Leu Lys Val Asp Leu Thr Lys Tyr
         35                  40                  45
Leu Glu Asn Gln Ala Phe Cys Phe Asp Phe Ala Phe Asp Glu Thr Ala
     50                  55                  60
Ser Asn Glu Val Val Tyr Arg Phe Thr Ala Arg Pro Leu Val Gln Thr
 65                  70                  75                  80
Ile Phe Glu Gly Gly Lys Ala Thr Cys Phe Ala Tyr Gly Gln Thr Gly
                 85                  90                  95
Ser Gly Lys Thr His Thr Met Gly Gly Asp Leu Ser Gly Lys Ala Gln
            100                 105                 110
Asn Ala Ser Lys Gly Ile Tyr Ala Met Ala Ser Arg Asp Val Phe Leu
        115                 120                 125
Leu Lys Asn Gln Pro Cys Tyr Arg Lys Leu Gly Leu Glu Val Tyr Val
    130                 135                 140
Thr Phe Phe Glu Ile Tyr Asn Gly Lys Leu Phe Asp Leu Leu Asn Lys
145                 150                 155                 160
Lys Ala Lys Leu Arg Val Leu Glu Asp Gly Lys Gln Gln Val Gln Val
                165                 170                 175
Val Gly Leu Gln Glu His Leu Val Asn Ser Ala Asp Asp Val Ile Lys
            180                 185                 190
```

```
Met Ile Asp Met Gly Ser Ala Cys Arg Thr Ser Gly Gln Thr Phe Ala
            195                 200                 205

Asn Ser Asn Ser Ser Arg Ser His Ala Cys Phe Gln Ile Ile Leu Arg
        210                 215                 220

Ala Lys Gly Arg Met His Gly Lys Phe Ser Leu Val Asp Leu Ala Gly
225                 230                 235                 240

Asn Glu Arg Gly Ala Asp Thr Ser Ser Ala Asp Arg Gln Thr Arg Met
                245                 250                 255

Glu Gly Ala Glu Ile Asn Lys Ser Leu Leu Ala Leu Lys Glu Cys Ile
            260                 265                 270

Arg Ala Leu Gly Gln Asn Lys Ala His Thr Pro Phe Arg Glu Ser Lys
        275                 280                 285

Leu Thr Gln Val Leu Arg Asp Ser Phe Ile Gly Glu Asn Ser Arg Thr
    290                 295                 300

Cys Met Ile Ala Thr Ile Ser Pro Gly Ile Ser Ser Cys Glu Tyr Thr
305                 310                 315                 320

Leu Asn Thr Leu Arg Tyr Ala Asp Arg Val Lys Glu Leu Ser Pro His
                325                 330                 335

Ser Gly Pro Ser Gly Glu Gln Leu Ile Gln Met Glu Thr Glu Glu Met
            340                 345                 350

Glu Ala Cys Ser Asn Gly Ala Leu Ile Pro Gly Asn Leu Ser Lys Glu
        355                 360                 365

Glu Glu Glu Leu Ser Ser Gln Met Ser Ser Phe Asn Glu Ala Met Thr
    370                 375                 380

Gln Ile Arg Glu Leu Glu Glu Lys Ala Met Glu Glu Leu Lys Glu Ile
385                 390                 395                 400

Ile Gln Gln Gly Pro
            405

<210> SEQ ID NO 13
<211> LENGTH: 2172
<212> TYPE: DNA
<213> ORGANISM: Human

<400> SEQUENCE: 13
atggactcgt cgcttcaggc ccgcctgttt cccggtctcg ctatcaagat ccaacgcagt      60
aatggtttaa ttcacagtgc caatgtaagg actgtgaact tggagaaatc ctgtgtttca     120
gtggaatggg cagaaggagg tgccacaaag ggcaaagaga ttgattttga tgatgtggct     180
gcaataaacc cagaactctt acagcttctt cccttacatc cgaaggacaa tctgcccttg     240
caggaaaatg taacaatcca gaaacaaaaa cggagatccg tcaactccaa aattcctgct     300
ccaaaagaaa gtcttcgaag ccgctccact cgcatgtcca ctgtctcaga gcttcgcatc     360
acggctcagg agaatgacat ggaggtggag ctgcctgcag ctgcaaactc cgcaagcag      420 ttttcagttc ctcctgcccc cactaggcct tcctgccctg cagtggctga ataccattg      480 aggatggtca gcgaggagat ggaagagcaa gtccattcca tccgtggcag ctcttctgca     540
aaccctgtga actcagttcg gaggaaatca tgtcttgtga aggaagtgga aaaaatgaag     600
aacaagcgag aagagaagaa ggcccagaac tctgaaatga aatgaagag agctcaggag      660 tatgacagta gttttccaaa ctgggaattt gcccgaatga ttaaagaatt tcgggctact     720
ttggaatgtc atccacttac tatgactgat cctatcgaag agcacagaat atgtgtctgt     780
gttaggaaac gcccactgaa taagcaagaa ttggccaaga agaaattga tgtgatttcc      840 attcctagca gtgtctcct cttggtacat gaacccaagt tgaaagtgga cttaacaaag     900
```

-continued

```
tatctggaga accaagcatt ctgctttgac tttgcatttg atgaaacagc ttcgaatgaa      960
gttgtctaca ggttcacagc aaggccactg gtacagacaa tctttgaagg tggaaaagca     1020
acttgttttg catatggcca gacaggaagt ggcaagacac atactatggg cggagacctc     1080
tctgggaaag cccagaatgc atccaaaggg atctatgcca tggcctcccg ggacgtcttc     1140
ctcctgaaga atcaaccctg ctaccggaag ttgggcctgg aagtctatgt gacattcttc     1200
gagatctaca atgggaagct gtttgacctg ctcaacaaga aggccaagct gcgcgtgctg     1260
gaggatggca agcaacaggt gcaagtggtg gggctgcagg agcatctggt taactctgct     1320
gatgatgtca tcaagatgat cgacatgggc agcgcctgca gaacctctgg gcagacattt     1380
gccaactcca attcctcccg ctcccacgcg tgcttccaaa ttattcttcg agctaaaggg     1440
agaatgcatg gcaagttctc tttggtagat ctggcaggga atgagcgagg cgcggacact     1500
tccagtgctg accggcagac ccgcatggag ggcgcagaaa tcaacaagag tctcttagcc     1560
ctgaaggagt gcatcagggc cctgggacag aacaaggctc acaccccgtt ccgtgagagc     1620
aagctgacac aggtgctgag ggactccttc attggggaga actctaggac ttgcatgatt     1680
gccacgatct caccaggcat aagctcctgt gaatatactt taaacaccct gagatatgca     1740
gacagggtca aggagctgag cccccacagt gggcccagtg gagagcagtt gattcaaatg     1800
gaaacagaag agatggaagc ctgctctaac ggggcgctga ttccaggcaa tttatccaag     1860
gaagaggagg aactgtcttc ccagatgtcc agctttaacg aagccatgac tcagatcagg     1920
gagctggagg agaaggctat ggaagagctc aaggagatca tacagcaagg accagactgg     1980
cttgagctct ctgagatgac cgagcagcca gactatgacc tggagacctt tgtgaacaaa     2040
gcggaatctg ctctggccca gcaagccaag catttctcag ccctgcgaga tgtcatcaag     2100
gccttacgcc tggccatgca gctggaagag caggctagca gacaaataag cagcaagaaa     2160
cggccccagt ga                                                          2172
```

<210> SEQ ID NO 14
<211> LENGTH: 723
<212> TYPE: PRT
<213> ORGANISM: Human

<400> SEQUENCE: 14

```
Met Asp Ser Ser Leu Gln Ala Arg Leu Phe Pro Gly Leu Ala Ile Lys
 1               5                  10                  15

Ile Gln Arg Ser Asn Gly Leu Ile His Ser Ala Asn Val Arg Thr Val
            20                  25                  30

Asn Leu Glu Lys Ser Cys Val Ser Val Glu Trp Ala Glu Gly Gly Ala
        35                  40                  45

Thr Lys Gly Lys Glu Ile Asp Phe Asp Asp Val Ala Ala Ile Asn Pro
    50                  55                  60

Glu Leu Leu Gln Leu Leu Pro Leu His Pro Lys Asp Asn Leu Pro Leu
65                  70                  75                  80

Gln Glu Asn Val Thr Ile Gln Lys Gln Lys Arg Ser Val Asn Ser
                85                  90                  95

Lys Ile Pro Ala Pro Lys Glu Ser Leu Arg Ser Arg Ser Thr Arg Met
            100                 105                 110

Ser Thr Val Ser Glu Leu Arg Ile Thr Ala Gln Glu Asn Asp Met Glu
        115                 120                 125

Val Glu Leu Pro Ala Ala Ala Asn Ser Arg Lys Gln Phe Ser Val Pro
    130                 135                 140
```

```
Pro Ala Pro Thr Arg Pro Ser Cys Pro Ala Val Ala Glu Ile Pro Leu
145                 150                 155                 160

Arg Met Val Ser Glu Glu Met Glu Glu Gln Val His Ser Ile Arg Gly
            165                 170                 175

Ser Ser Ser Ala Asn Pro Val Asn Ser Val Arg Arg Lys Ser Cys Leu
            180                 185                 190

Val Lys Glu Val Glu Lys Met Lys Asn Lys Arg Glu Lys Lys Ala
        195                 200                 205

Gln Asn Ser Glu Met Arg Met Lys Arg Ala Gln Glu Tyr Asp Ser Ser
        210                 215                 220

Phe Pro Asn Trp Glu Phe Ala Arg Met Ile Lys Glu Phe Arg Ala Thr
225                 230                 235                 240

Leu Glu Cys His Pro Leu Thr Met Thr Asp Pro Ile Glu Glu His Arg
                245                 250                 255

Ile Cys Val Cys Val Arg Lys Arg Pro Leu Asn Lys Gln Glu Leu Ala
            260                 265                 270

Lys Lys Glu Ile Asp Val Ile Ser Ile Pro Ser Lys Cys Leu Leu Leu
        275                 280                 285

Val His Glu Pro Lys Leu Lys Val Asp Leu Thr Lys Tyr Leu Glu Asn
    290                 295                 300

Gln Ala Phe Cys Phe Asp Phe Ala Phe Asp Glu Thr Ala Ser Asn Glu
305                 310                 315                 320

Val Val Tyr Arg Phe Thr Ala Arg Pro Leu Val Gln Thr Ile Phe Glu
                325                 330                 335

Gly Gly Lys Ala Thr Cys Phe Ala Tyr Gly Gln Thr Gly Ser Gly Lys
            340                 345                 350

Thr His Thr Met Gly Gly Asp Leu Ser Gly Lys Ala Gln Asn Ala Ser
        355                 360                 365

Lys Gly Ile Tyr Ala Met Ala Ser Arg Asp Val Phe Leu Leu Lys Asn
    370                 375                 380

Gln Pro Cys Tyr Arg Lys Leu Gly Leu Glu Val Tyr Val Thr Phe Phe
385                 390                 395                 400

Glu Ile Tyr Asn Gly Lys Leu Phe Asp Leu Leu Asn Lys Lys Ala Lys
                405                 410                 415

Leu Arg Val Leu Glu Asp Gly Lys Gln Gln Val Gln Val Val Gly Leu
            420                 425                 430

Gln Glu His Leu Val Asn Ser Ala Asp Val Ile Lys Met Ile Asp
        435                 440                 445

Met Gly Ser Ala Cys Arg Thr Ser Gly Gln Thr Phe Ala Asn Ser Asn
450                 455                 460

Ser Ser Arg Ser His Ala Cys Phe Gln Ile Ile Leu Arg Ala Lys Gly
465                 470                 475                 480

Arg Met His Gly Lys Phe Ser Leu Val Asp Leu Ala Gly Asn Glu Arg
                485                 490                 495

Gly Ala Asp Thr Ser Ser Ala Asp Arg Gln Thr Arg Met Glu Gly Ala
            500                 505                 510

Glu Ile Asn Lys Ser Leu Leu Ala Leu Lys Glu Cys Ile Arg Ala Leu
        515                 520                 525

Gly Gln Asn Lys Ala His Thr Pro Phe Arg Glu Ser Lys Leu Thr Gln
    530                 535                 540

Val Leu Arg Asp Ser Phe Ile Gly Glu Asn Ser Arg Thr Cys Met Ile
545                 550                 555                 560
```

Ala Thr Ile Ser Pro Gly Ile Ser Ser Cys Glu Tyr Thr Leu Asn Thr
            565                 570                 575

Leu Arg Tyr Ala Asp Arg Val Lys Glu Leu Ser Pro His Ser Gly Pro
        580                 585                 590

Ser Gly Glu Gln Leu Ile Gln Met Glu Thr Glu Glu Met Glu Ala Cys
    595                 600                 605

Ser Asn Gly Ala Leu Ile Pro Gly Asn Leu Ser Lys Glu Glu Glu
    610                 615                 620

Leu Ser Ser Gln Met Ser Ser Phe Asn Glu Ala Met Thr Gln Ile Arg
625                 630                 635                 640

Glu Leu Glu Glu Lys Ala Met Glu Glu Leu Lys Glu Ile Ile Gln Gln
                645                 650                 655

Gly Pro Asp Trp Leu Glu Leu Ser Glu Met Thr Glu Gln Pro Asp Tyr
            660                 665                 670

Asp Leu Glu Thr Phe Val Asn Lys Ala Glu Ser Ala Leu Ala Gln Gln
        675                 680                 685

Ala Lys His Phe Ser Ala Leu Arg Asp Val Ile Lys Ala Leu Arg Leu
    690                 695                 700

Ala Met Gln Leu Glu Glu Gln Ala Ser Arg Gln Ile Ser Ser Lys Lys
705                 710                 715                 720

Arg Pro Gln

<210> SEQ ID NO 15
<211> LENGTH: 2740
<212> TYPE: DNA
<213> ORGANISM: Human

<400> SEQUENCE: 15

```
gcgaaattga ggtttcttgg tattgcgcgt ttctcttcct tgctgactct ccgaatggcc     60
atggactcgt cgcttcaggc ccgcctgttt cccggtctcg ctatcaagat ccaacgcagt    120
aatggtttaa ttcacagtgc caatgtaagg actgtgaact ggagaaatc ctgtgtttca    180
gtggaatggg cagaaggagg tgccacaaag ggcaaagaga ttgattttga tgatgtggct    240
gcaataaacc cagaactctt acagcttctt cccttacatc cgaaggacaa tctgcccttg    300
caggaaaatg taacaatcca gaaacaaaaa cggagatccg tcaactccaa aattcctgct    360
ccaaaagaaa gtcttcgaag ccgctccact cgcatgtcca ctgtctcaga gcttcgcatc    420
acggctcagg agaatgacat ggaggtggag ctgcctgcag ctgcaaactc ccgcaagcag    480
ttttcagttc ctcctgcccc cactaggcct tcctgccctg cagtggctga ataccattg    540
aggatggtca gcgaggagat ggaagagcaa gtccattcca tccgtggcag ctcttctgca    600
aaccctgtga actcagttcg gaggaaatca tgtcttgtga aggaagtgga aaaaatgaag    660
aacaagcgag aagagaagaa ggcccagaac tctgaaatga aatgaagag agctcaggag    720
tatgacagta gttttccaaa ctgggaattt gcccgaatga ttaaagaatt cgggctact    780
ttggaatgtc atccacttac tatgactgat cctatcgaag agcacagaat atgtgtctgt    840
gttaggaaac gcccactgaa taagcaagaa ttggccaaga agaaattga tgtgatttcc    900
attcctagca agtgtctcct cttggtacat gaacccaagt tgaaagtgga cttaacaaag    960
tatctggaga ccaagcatt ctgctttgac tttgcatttg atgaaacagc ttcgaatgaa   1020
gttgtctaca ggttcacagc aaggccactg tacagacaa tctttgaagg tggaaaagca   1080
acttgttttg catatggcca gacaggaagt ggcaagacac atactatggg cggagaccctc  1140
tctgggaaag cccagaatgc atccaaaggg atctatgcca tggcctcccg ggacgtcttc   1200
```

-continued

```
ctcctgaaga atcaaccctg ctaccggaag ttgggcctgg aagtctatgt gacattcttc    1260
gagatctaca atgggaagct gttttgacctg ctcaacaaga aggccaagct gcgcgtgctg    1320
gaggacggca agcaacaggt gcaagtggtg gggctgcagg agcatctggt taactctgct    1380
gatgatgtca tcaagatgct cgacatgggc agcgcctgca gaacctctgg gcagacattt    1440
gccaactcca attcctcccg ctcccacgcg tgcttccaaa ttattcttcg agctaaaggg    1500
agaatgcatg gcaagttctc tttggtagat ctggcaggga atgagcgagg cgcagacact    1560
tccagtgctg accggcagac ccgcatgag ggcgcagaaa tcaacaagag tctcttagcc    1620
ctgaaggagt gcatcagggc cctgggacag aacaaggctc acaccccgtt ccgtgagagc    1680
aagctgacac aggtgctgag ggactccttc attggggaga actctaggac ttgcatgatt    1740
gccacgatct caccaggcat aagctcctgt gaatatactt taaacaccct gagatatgca    1800
gacagggtca aggagctgag cccccacagt gggcccagtg agagcagtt gattcaaatg    1860 gaaacagaag agatggaagc ctgctctaac ggggcgctga ttccaggcaa tttatccaag    1920
gaagaggagg aactgtcttc ccagatgtcc agctttaacg aagccatgac tcagatcagg    1980
gagctggagg agaaggctat ggaagagctc aaggagatca tacagcaagg accagactgg    2040
cttgagctct ctgagatgac cgagcagcca gactatgacc tggagacctt tgtgaacaaa    2100
gcggaatctg ctctggccca gcaagccaag catttctcag ccctgcgaga tgtcatcaag    2160
gccttacgcc tggccatgca gctggaagag caggctagca gacaaataag cagcaagaaa    2220
cggccccagt gacgactgca aataaaaatc tgtttggttt gacacccagc ctcttccctg    2280
gccctcccca gagaactttg ggtacctggt gggtctaggc agggtctgag ctgggacagg    2340
ttctggtaaa tgccaagtat gggggcatct gggcccaggg cagctgggga ggggtcaga    2400 gtgacatggg acactccttt tctgttcctc agttgtcgcc ctcacgagag aaggagctc    2460 ttagttaccc ttttgtgttg cccttctttc catcaagggg aatgttctca gcatagagct    2520
ttctccgcag catcctgcct gcgtggactg gctgctaatg gagagctccc tggggttgtc    2580
ctggctctgg ggagagagac ggagcctttta gtacagctat ctgctggctc taaaccttct    2640
acgcctttgg gccgagcact gaatgtcttg tactttaaaa aaatgtttct gagacctctt    2700
tctactttac tgtctcccta gagtcctaga ggatccctac                          2740
```

<210> SEQ ID NO 16
<211> LENGTH: 725
<212> TYPE: PRT
<213> ORGANISM: Human

<400> SEQUENCE: 16

```
Met Ala Met Asp Ser Ser Leu Gln Ala Arg Leu Phe Pro Gly Leu Ala
 1               5                  10                  15

Ile Lys Ile Gln Arg Ser Asn Gly Leu Ile His Ser Ala Asn Val Arg
            20                  25                  30

Thr Val Asn Leu Glu Lys Ser Cys Val Ser Val Glu Trp Ala Glu Gly
        35                  40                  45

Gly Ala Thr Lys Gly Lys Glu Ile Asp Phe Asp Val Ala Ala Ile
    50                  55                  60

Asn Pro Glu Leu Leu Gln Leu Leu Pro Leu His Pro Lys Asp Asn Leu
65                  70                  75                  80

Pro Leu Gln Glu Asn Val Thr Ile Gln Lys Gln Lys Arg Arg Ser Val
                85                  90                  95
```

```
Asn Ser Lys Ile Pro Ala Pro Lys Glu Ser Leu Arg Ser Arg Ser Thr
            100                 105                 110
Arg Met Ser Thr Val Ser Glu Leu Arg Ile Thr Ala Gln Glu Asn Asp
        115                 120                 125
Met Glu Val Glu Leu Pro Ala Ala Asn Ser Arg Lys Gln Phe Ser
    130                 135                 140
Val Pro Ala Pro Thr Arg Pro Ser Cys Pro Ala Val Ala Glu Ile
145                 150                 155                 160
Pro Leu Arg Met Val Ser Glu Met Glu Glu Gln Val His Ser Ile
                165                 170                 175
Arg Gly Ser Ser Ser Ala Asn Pro Val Asn Ser Val Arg Arg Lys Ser
            180                 185                 190
Cys Leu Val Lys Glu Val Glu Lys Met Lys Asn Lys Arg Glu Glu Lys
        195                 200                 205
Lys Ala Gln Asn Ser Glu Met Arg Met Lys Arg Ala Gln Glu Tyr Asp
    210                 215                 220
Ser Ser Phe Pro Asn Trp Glu Phe Ala Arg Met Ile Lys Glu Phe Arg
225                 230                 235                 240
Ala Thr Leu Glu Cys His Pro Leu Thr Met Thr Asp Pro Ile Glu Glu
                245                 250                 255
His Arg Ile Cys Val Cys Val Arg Lys Arg Pro Leu Asn Lys Gln Glu
            260                 265                 270
Leu Ala Lys Lys Glu Ile Asp Val Ile Ser Ile Pro Ser Lys Cys Leu
        275                 280                 285
Leu Leu Val His Glu Pro Lys Leu Lys Val Asp Leu Thr Lys Tyr Leu
    290                 295                 300
Glu Asn Gln Ala Phe Cys Phe Asp Phe Ala Phe Asp Glu Thr Ala Ser
305                 310                 315                 320
Asn Glu Val Val Tyr Arg Phe Thr Ala Arg Pro Leu Val Gln Thr Ile
                325                 330                 335
Phe Glu Gly Gly Lys Ala Thr Cys Phe Ala Tyr Gly Gln Thr Gly Ser
            340                 345                 350
Gly Lys Thr His Thr Met Gly Gly Asp Leu Ser Gly Lys Ala Gln Asn
        355                 360                 365
Ala Ser Lys Gly Ile Tyr Ala Met Ala Ser Arg Asp Val Phe Leu Leu
    370                 375                 380
Lys Asn Gln Pro Cys Tyr Arg Lys Leu Gly Leu Glu Val Tyr Val Thr
385                 390                 395                 400
Phe Phe Glu Ile Tyr Asn Gly Lys Leu Phe Asp Leu Leu Asn Lys Lys
                405                 410                 415
Ala Lys Leu Arg Val Leu Glu Asp Gly Lys Gln Gln Val Gln Val Val
            420                 425                 430
Gly Leu Gln Glu His Leu Val Asn Ser Ala Asp Val Ile Lys Met
        435                 440                 445
Leu Asp Met Gly Ser Ala Cys Arg Thr Ser Gly Gln Thr Phe Ala Asn
    450                 455                 460
Ser Asn Ser Ser Arg Ser His Ala Cys Phe Gln Ile Ile Leu Arg Ala
465                 470                 475                 480
Lys Gly Arg Met His Gly Lys Phe Ser Leu Val Asp Leu Ala Gly Asn
                485                 490                 495
Glu Arg Gly Ala Asp Thr Ser Ser Ala Asp Arg Gln Thr Arg Met Glu
            500                 505                 510
Gly Ala Glu Ile Asn Lys Ser Leu Leu Ala Leu Lys Glu Cys Ile Arg
```

-continued

```
            515                 520                 525
Ala Leu Gly Gln Asn Lys Ala His Thr Pro Phe Arg Glu Ser Lys Leu
        530                 535                 540

Thr Gln Val Leu Arg Asp Ser Phe Ile Gly Glu Asn Ser Arg Thr Cys
545                 550                 555                 560

Met Ile Ala Thr Ile Ser Pro Gly Ile Ser Ser Cys Glu Tyr Thr Leu
                565                 570                 575

Asn Thr Leu Arg Tyr Ala Asp Arg Val Lys Glu Leu Ser Pro His Ser
                580                 585                 590

Gly Pro Ser Gly Glu Gln Leu Ile Gln Met Glu Thr Glu Glu Met Glu
            595                 600                 605

Ala Cys Ser Asn Gly Ala Leu Ile Pro Gly Asn Leu Ser Lys Glu Glu
        610                 615                 620

Glu Glu Leu Ser Ser Gln Met Ser Ser Phe Asn Glu Ala Met Thr Gln
625                 630                 635                 640

Ile Arg Glu Leu Glu Glu Lys Ala Met Glu Glu Leu Lys Glu Ile Ile
                645                 650                 655

Gln Gln Gly Pro Asp Trp Leu Glu Leu Ser Glu Met Thr Glu Gln Pro
                660                 665                 670

Asp Tyr Asp Leu Glu Thr Phe Val Asn Lys Ala Glu Ser Ala Leu Ala
                675                 680                 685

Gln Gln Ala Lys His Phe Ser Ala Leu Arg Asp Val Ile Lys Ala Leu
            690                 695                 700

Arg Leu Ala Met Gln Leu Glu Glu Gln Ala Ser Arg Gln Ile Ser Ser
705                 710                 715                 720

Lys Lys Arg Pro Gln
                725
```

MOTOR PROTEINS AND METHODS FOR THEIR USE

CROSS REFERENCE TO RELATED APPLICATIONS

The present application is a continuation of U.S. application Ser. No. 09/724,215, filed Nov. 28, 2000 now abandoned, which is incorporated herein by reference.

FIELD OF THE INVENTION

The invention relates to methods for the identification of compounds that modulate the activity of target proteins having motor domains and use of such methods for the identification of therapeutic agents.

BACKGROUND OF THE INVENTION

The kinesin superfamily is an extended family of related microtubule motor proteins. It can be classified into at least 8 subfamilies based on primary amino acid sequence, domain structure, velocity of movement, and cellular function. This family is exemplified by "true" kinesin, which was first isolated from the axoplasm of squid, where it is believed to play a role in anterograde axonal transport of vesicles and organelles (see, e.g., Goldstein, Annu. Rev. Genet. 27:319–351(1993)).

Mitotic kinesins are enzymes essential for assembly and function of the mitotic spindle, but are not generally part of other microtubule structures. Mitotic kinesins play essential roles during all phases of mitosis. These enzymes are "molecular motors" that translate energy released by hydrolysis of ATP into mechanical force which drives the directional movement of cellular cargoes along microtubules. The catalytic domain sufficient for this task is a compact structure of approximately 340 amino acids. During mitosis, kinesins organize microtubules into the bipolar spindle that is the mitotic spindle. Kinesins mediate movement of chromosomes along spindle microtubules, as well as structural changes in the mitotic spindle associated with specific phases of mitosis. Experimental perturbation of mitotic kinesin function causes malformation or dysfunction of the mitotic spindle, frequently resulting in cell cycle arrest.

Within this functional group of kinesins resides a group of kinesins from several organisms that share significant sequence homology, the Kin I subfamily, and that function to destabilize microtubule ends. These include H. sapiens MCAK (also known as mitotic centromere-associated kinesin orHsMCAK), X laevis MCAK, and C. griseus MCAK.

During anaphase A, disjoined sister chromatids migrate poleward. This poleward movement is driven by kinetochores and is accompanied by the depolymerization of microtubules attached to the migrating chromatids. The kinesin MCAK plays an important role in this motility and may promote disassembly of microtubules attached to kinetochores of mitotic chromosomes.

The HsMCAK gene has a predicted 723 amino acid open reading frame, encoding a 81 kDa protein that shares 79.2% homology with hamster MCAK. HsMCAK is expressed in tissues containing dividing cells, such as thymus, testis, small intestine, colon (mucosal lining), and placenta. Genes for the Xenopus and hamster homologs of MCAK has also been cloned and characterized.

Defects in function of these proteins would be expected to result in cell cycle arrest in mitosis. As such, compounds that modulate the activity of these kinesins may affect cellular proliferation. The present invention provides a novel method to identify such compounds.

SUMMARY OF THE INVENTION

The present invention provides methods to identify candidate agents that bind to a target protein or act as a modulator of the binding characteristics or biological activity of a target protein. In one embodiment, the method is performed in plurality simultaneously.

For example, the method can be performed at the same time on multiple assay mixtures in a multi-well screening plate. Furthermore, in a preferred embodiment, fluorescence or absorbance readouts are utilized to determine activity. Thus, in one aspect, the invention provides a high throughput screening system for detecting modulators of activity a target protein.

In one embodiment, the present invention provides a method of identifying a candidate agent as a modulator of the activity of a target protein. The method comprises adding a candidate agent to a mixture comprising a target protein which directly or indirectly produces ADP or phosphate, under conditions that normally allow the production of ADP or phosphate. The method further comprises subjecting the mixture to a reaction that uses said ADP or phosphate as a substrate under conditions that normally allow the ADP or phosphate to be utilized and determining the level of activity of the reaction as a measure of the concentration of ADP or phosphate. A change in the level between the presence and absence of the candidate agent indicates a modulator of the target protein.

The phrase "use ADP or phosphate" means that the ADP or phosphate are directly acted upon by detection reagents. In one case, the ADP, for example, can be hydrolyzed or can be phosphorylated. As another example, the phosphate can be added to another compound. As used herein, in each of these cases, ADP or phosphate is acting as a substrate.

Preferably, the target protein either directly or indirectly produces ADP or phosphate and comprises a motor domain. More preferably, the target protein comprises HsMCAK, X laevis MCAK, and C. griseus MCAK or a fragment thereof. Most preferably, the target protein comprises SEQ ID NO:2, SEQ ID NO:4, SEQ ID NO:6, SEQ ID NO:8, SEQ ID NO:10, SEQ ID NO:12, or SEQ ID NO:14.

Also provided are modulators of the target protein including agents for the treatment of cellular proliferation, including cancer, hyperplasias, restenosis, cardiac hypertrophy, immune disorders and inflammation. The agents and compositions provided herein can be used in variety of applications which include the formulation of sprays, powders, and other compositions. Also provided herein are methods of treating cellular proliferation disorders such as cancer, hyperplasias, restenosis, cardiac hypertrophy, immune disorders and inflammation, for treating disorders associated with MCAK activity, and for inhibiting MCAK.

BRIEF DESCRIPTION OF THE DRAWINGS

FIG. 1 shows an embodiment of a nucleic acid sequence encoding a particularly preferred target protein (SEQ ID NO:9:1).

FIG. 2 shows an embodiment of a particularly preferred target protein (SEQ ID NO:2). The construct contains residues 189 through 617 of the full length MCAK enzyme.

FIG. 3 shows an embodiment of a nucleic acid sequence encoding a particularly preferred target protein (SEQ ID NO:3).

FIG. 4 shows an embodiment of another particularly preferred target protein (SEQ ID NO:4). The construct contains residues 228 through 617 of the full length MCAK enzyme.

FIG. 5 shows an embodiment of a nucleic acid sequence encoding a particularly preferred target protein (SEQ ID NO:5).

FIG. 6 shows an embodiment of another particularly preferred target protein (SEQ ID NO:6). The construct contains residues 257 through 617 of the full length MCAK enzyme.

FIG. 7 shows an embodiment of a nucleic acid sequence encoding a particularly preferred target protein (SEQ ID NO:7).

FIG. 8 shows an embodiment of a particularly preferred target protein (SEQ ID NO:8). The construct contains residues 189 through 660 of the full length MCAK enzyme.

FIG. 9 shows an embodiment of a nucleic acid sequence encoding a particularly preferred target protein (SEQ ID NO:9).

FIG. 10 shows an embodiment of a particularly preferred target protein (SEQ ID NO:10). The construct contains residues 228 through 660 of the full length MCAK enzyme.

FIG. 11 shows an embodiment of a nucleic acid sequence encoding a particularly preferred target protein (SEQ ID NO:11).

FIG. 12 shows an embodiment of a particularly preferred target protein (SEQ ID NO:12). The construct contains residues 257 through 660 of the full length MCAK enzyme.

FIG. 13 shows an embodiment of a nucleic acid sequence encoding a particularly preferred target protein (SEQ ID NO:13).

FIG. 14 shows an embodiment of a particularly preferred target protein (SEQ ID NO:14). The constrict contains residues 3 through 725 of the full length MCAK enzyme.

FIGS. 15 A and B show a nucleic acid sequence encoding HsMCAK (SEQ ID NO:15).

FIG. 16 shows the amino acid sequence of HsMCAK (SEQ ID NO:16).

DETAILED DESCRIPTION OF THE INVENTION

I. Definitions

"ADP" refers to adenosine diphosphate and also includes ADP analogs, including, but not limited to, deoxyadenosine diphosphate (dADP) and adenosine analogs.

"Biologically active" target protein refers to a target protein that has one or more of kinesin protein's biological activities, including, but not limited to microtubule stimulated ATPase activity, as tested, e.g., in an ATPase assay. Biological activity can also be demonstrated in a microtubule gliding assay or a microtubule binding assay. "ATPase activity" refers to ability to hydrolyze ATP. Other activities include polymerization/depolymerization (effects on microtubule dynamics), binding to other proteins of the spindle, binding to proteins involved in cell-cycle control, or serving as a substrate to other enzymes, such as kinases or proteases and specific kinesin cellular activities, such as chromosome congregation, axonal transport, etc.

"Biological sample" as used herein is a sample of biological tissue or fluid that contains a target protein or a fragment thereof or nucleic acid encoding a target protein or a fragment thereof. Biological samples may also include sections of tissues such as frozen sections taken for histological purposes. A biological sample comprises at least one cell, preferably plant or vertebrate. Embodiments include cells obtained from a eukaryotic organism, preferably eukaryotes such as fungi, plants, insects, protozoa, birds, fish, reptiles, and preferably a mammal such as rat, mice, cow, dog, guinea pig, or rabbit, and most preferably a primate such as chimpanzees or humans.

A "comparison window" includes reference to a segment of any one of the number of contiguous positions selected from the group consisting of from 25 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the global alignment algorithm of Needleman & Wunsch, J. Mol. Biol. 48:443 (1970), by the search for similarity methods of Pearson & Lipman, Proc. Natl. Acad. Sci. USA 85:2444 (1988) and Altschul et al. Nucleic Acids Res. 25(17): 3389–3402 (1997), by computerized implementations of these algorithms (GAP, BESTFIT, FASTA, and BLAST in the Wisconsin Genetics Software Package, Genetics Computer Group, 575 Science Dr., Madison, Wis.), or by manual alignment and visual inspection (see, e.g., Ausubel et al., supra).

One example of a useful algorithm is PILEUP. PILEUP creates a multiple sequence alignment from a group of related sequences using progressive, pairwise alignments. It can also plot a dendrogram showing the clustering relationships used to create the alignment. PILEUP uses a simplification of the progressive alignment method of Feng & Doolittle, J. Mol. Evol. 35:351–360 (1987). The method used is similar to the method described by Higgins & Sharp, CABIOS 5:151–153 (1989). As a general rule, PileUp can align up to 500 sequences, with any single sequence in the final alignment restricted to a maximum length of 7,000 characters.

The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. A series of such pairwise alignments that includes increasingly dissimilar sequences and clusters of sequences at each iteration produces the final alignment.

"Variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCT all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each degenerate codon in a nucleic acid can be modlified to yield a functionally identical molecule. Accordingly, each silent variation of a nucleic acid which encodes a polypeptide is implicit in each described sequence.

Also included within the definition of target proteins of the present invention are amino acid sequence variants of wild-type target proteins. These variants fall into one or more of three classes: substitutional, insertional or deletional variants. These variants ordinarily are prepared by site specific mutagenesis of nucleotides in the DNA encoding the target protein, using cassette or PCR mutagenesis or other techniques well known in the art, to produce DNA encoding the variant, and thereafter expressing the DNA in recombinant cell culture. Variant target protein fragments having up to about 100–150 amino acid residues may be prepared by in vitro synthesis using established techniques. Amino acid sequence variants are characterized by the predetermined nature of the variation, a feature that sets them apart from naturally occurring allelic or interspecies variation of the target protein amino acid sequence. The variants typically exhibit the same qualitative biological activity as the naturally occurring analogue, although variants can also be selected which have modified characteristics.

Amino acid substitutions are typically of single residues; insertions usually will be on the order of from about 1 to about 20 amino acids, although considerably longer insertions may be tolerated. Deletions range from about 1 to about 20 residues, although in some cases, deletions may be much longer.

Substitutions, deletions, and insertions or any combinations thereof may be used to arrive at a final derivative. Generally, these changes are done on a few amino acids to minimize the alteration of the molecule. However, larger characteristics may be tolerated in certain circumstances.

The following six groups each contain, amino acids that are conservative substitutions for one another:
1) Alanine (A), Serine (S), Theonine (T);
2) Aspartic acid (D), Glutamic acid (E);
3) Asparagine (N), Glutamine (Q);
4) Arginine (R), Lysine (K);
5) Isoleucine (1), Leucine (L), Methionine (M), Valine (V); and
6) Phenylalanine (F), Tyrosine (Y), Tryptophan (W).
(see, e.g., Creighton, Proteins (1984)).

"Cytoskeletal component" denotes any molecule that is found in association with the cellular cytoskeleton, that plays a role in maintaining or regulating the structural integrity of the cytoskeleton, or that mediates or regulates motile events mediated by the cytoskeleton. Includes cytoskeletal polymers (e.g., actin filaments, microtubules, intermediate filaments, myosin fragments), molecular motors (e.g., kinesins, myosins, dyneins), cytoskeleton associated regulatory proteins (e.g., tropomysin, alpha-actinin) and cytoskeletal associated binding proteins (e.g., microtubules associated proteins, actin binding proteins).

"Cytoskeletal function" refers to biological roles of the cytoskeleton, including but not limited to the providing of structural organization (e.g., microvilli, mitotic spindle) and the mediation of motile events within the cell (e.g., muscle contraction, mitotic chromosome movements, contractile ring formation and function, pseudopodal movement, active cell surface deformations, vesicle formation and translocation.)

A "diagnostic" as used herein is a compound, method, system, or device that assists in the identification and characterization of a health or disease state. The diagnostic can be used in standard assays as is known in the art.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

"High stringency conditions" may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"High throughput screening" as used herein refers to an assay which provides for multiple candidate agents or samples to be screened simultaneously. As further described below, examples of such assays may include the use of microtiter plates which are especially convenient because a large number of assays can be carried out simultaneously, using small amounts of reagents and samples.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, or plant cells. Both primary cells and cultured cell lines are included in this definition.

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. Stringent conditions are sequence-dependent and will be different in different circumstances. Longer sequences hybridize specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength, pH, and nucleic acid concentration) at which 50% of the probes complementary to the target sequence hybridize to the target sequence at equilibrium. Typically, stringent conditions will be those in which the salt concentration is less than about 1.0 M sodium ion, typically about 0.05 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

The terms "identical" or percent "identity", in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. Preferably, the percent identity exists over a region of the sequence that is at least about 25 amino acids in length, more preferably over a region that is 50 or 100 amino acids in length. This definition also refers to the complement of a test sequence, provided that the test sequence has a designated or substantial identity to a reference sequence. Preferably, the percent identity exists over a region of the sequence that is at least about 25 nucleotides in length, more preferably over a region that is 50 or 100 nucleotides in length.

When percentage of sequence identity is used in reference to proteins or peptides, it is recognized that residue positions that are not identical often differ by conservative amino acid substitutions, where amino acid residues are substituted for other amino acid residues with similar chemical properties (e.g,. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. The scoring of conservative substitutions can be calculated according to, e.g., the algorithm of Meyers & Millers, Computer Applic. Biol. Sci. 4:11–17 (1988), e.g., as implemented in the program PC/GENE (Intelligenetics, Mountain View, Calif.).

The terms "isolated", "purified", or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In an isolated target gene, the nucleic acid of interest is separated from open reading frames which flank the target gene and encode proteins other than the target protein. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

A "label" is a composition detectable by spectroscopic, photochemical, biochemical, immunochemical, or chemical means. For example, useful labels include fluorescent proteins such as green, yellow, red or blue fluorescent proteins, radioisotopes such as $^{32}P$, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO:2 can be made detectable, e.g., by incorporating a radio-label into the peptide, and used to detect antibodies specifically reactive with the peptide).

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and %SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 µg/mL denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

"Modulators," "inhibitors," and "activators of a target protein" refer to modulatory molecules identified using in vitro and in vivo assays for target protein activity. Such assays include ATPase activity, microtubule gliding, microtubule depolymerizing activity, and binding activity such as microtubule binding activity or binding of nucleotide analogs. Samples or assays that are treated with a candidate agent at a test and control concentration. The control concentration can be zero. If there is a change in target protein activity between the two concentrations, this change indicates the identification of a modulator. A change in activity, which can be an increase or decrease, is preferably a change of at least 20% to 50%, more preferably by at least 50% to 75%, more preferably at least 75% to 100%, and more preferably 150% to 200%, and most preferably is a change of at least 2 to 10 fold compared to a control. Additionally, a change can be indicated by a change in binding specificity or substrate.

"Molecular motor" refers to a molecule that utilizes chemical energy to generate mechanical force. According to one embodiment, the molecular motor drives the motile properties of the cytoskeleton.

The phrase "motor domain" refers to the domain to a target protein that confers membership in the kinesin superfamily of motor proteins through a sequence identity of approximately 35–45% identity to the motor domain of true kinesin.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. For example, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260)2605–2608 (1985); Cassol et al. 1992; Rossolini et al. Mol. Cell. Probes 8:91–98 (1994)). The term nucleic acid is used interchangeably with gene, cDNA, and mRNA encoded by a gene.

"Nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases. In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled with isotopes, chromophores, lumiphores, chromogens, or indirectly labeled such as with biotin to which a streptavidine complex may later bind. By assaying for the presence or absence of the probe, one can detect the presence or absence of the select sequence or subsequence.

The terms "polypeptide", "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers. A target protein comprises a polypeptide demonstrated to have at least microtubule stimulated ATPase activity. Amino acids may be referred to herein by either their commonly known three letter symbols or by Nomenclature Commission. Nucleotides, likewise, may be referred to by their commonly accepted single-letter codes, i.e., the one-letter symbols recommended by the IUPAC-IUB.

A "promoter" is defined as an array of nucleic acid control sequences that direct transcription of a nucleic acid. As used herein, a promoter includes necessary nucleic acid sequences near the start site of transcription, such as, in the case of a polymerase U type promoter, a TATA box element. A promoter also optionally includes distal enhancer or repressor elements which can be located as much as several thousand base pairs from the start site of transcription. A "constitutive" promoter is a promoter that is active under most environmental and developmental conditions. An "inducible" promoter is a promoter that is under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The phrase "specifically (or selectively) binds" to an antibody or "specifically (or selectively) immnunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, antibodies raised to the target protein with the amino acid sequence encoded in SEQ ID NO:2 can be selected to obtain only those antibodies that are specifically immunoreactive with the target protein and not with other proteins, except for polymorphic variants, orthologs, alleles, and closely related homologues of MCAK. This selection may be achieved by subtracting out antibodies that cross react with molecules, for example, such as C. elegans unc-104 and human Kifl A. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of inununoassay formats and conditions that can be used to determine specific immnunoreactive). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

"Test composition" (used interchangeably herein with "candidate agent" and "test compound" and "test agent") refers to a molecule or composition whose effect on the interaction between one or more cytoskeletal components it is desired to assay. The "test composition" can be any molecule or mixture of molecules, optionally in a carrier.

A "therapeutic" as used herein refers to a compound which is believed to be capable of modulating the cytoskeletal system in vivo which can have application in both human and animal disease. Modulation of the cytoskeletal system would be desirable in a number of conditions including, but not limited to: abnormal stimulation of endothelial cells (e.g., atherosclerosis), solid and hematopoetic tumors and tumor metastasis, benign tumors, for example, hemangiomas, acoustic neuromas, neurofibromas, pyogenic granulomas, vascular malfunctions, abnormal wound healing, inflammatory and immune disorders such as rheumatoid arthritis, Bechet's disease, gout or gouty arthritis, abnormal angiogenesis accompanying: rheumatoid arthritis, psoriasis, diabetic retinopathy, and other ocular angiogenic disease such as, macular degeneration, corneal graft rejection, corneal overgrowth, glaucoma, and Osler Webber syndrome.

II. The Target Protein

According to the present invention, a target protein is a molecule that either directly or indirectly produces ADP or phosphate and that comprises a motor domain. In a preferred embodiment, the target protein is an enzyme having activity which produces ADP and/or phosphate as a reaction product. Also included within the definition of the target proteins are amino acid sequence variants of wild-type target proteins.

Target proteins of the present invention may also be modified in a way to form chimeric molecules comprising a fusion of a target protein with a tag polypeptide which provides an epitope to which an anti-tag antibody can selectively bind. The epitope tag is generally placed at the amino or carboxyl terminus of the target protein. Provision of the epitope tag enables the target protein to be readily detected, as well as readily purified by affinity purification. Various tag epitopes are well known in the art. Examples include poly-histidine (poly-his) or poly-histidine-glycine (poly-his-gly) tags; the flu HA tag polypeptide and its antibody 12CA5 (see, Field et al. (1988) Mol. Cell. Biol. 8:2159); the c-myc tag and the 8F9, 3C7, 6E10, G4, B7 and 9E10 antibodies thereto (see, Evans et al., (1985) Molecular and Cellular Biology, 5:3610); and the Herpes Simplex virus glycoprotein D (gD) tag and its antibody (see, Paborsky et al., (1990) Protein Engineering, 3:547). Other tag polypeptides include the Flag-peptide (see, Hopp et al. (1988) BioTechnology 6:1204); the KT3 epitope peptide (see, Martine et al. (1992) Science, 255:192); tubulin epitope peptide (see, Skinner (1991) J. Biol. Chem. 266:15173); and the T7 gene 10 protein peptide tag (see, Lutz-Freyermuth et al. (1990) Proc. Natl. Acad. Sci. USA 87:6393. Target proteins of the present invention are meant to include both the untagged target protein as well as the chimeric protein wherein the target protein has been fused to one or more tag epitopes.

In a particularly preferred embodiment, the target protein comprises HsMCAK, X laevis MCAK, and C. griseus MCAK or a fragment thereof.

In another aspect of this invention, the target protein comprises an amino acid sequence which has greater than 70% sequence identity with SEQ ID NO:2, SEQ ID NO:4, SEQ ID NO:6, SEQ ID NO:8, SEQ ID NO:10, SEQ ID NO:12, or SEQ ID NO:14, preferably greater than 80%, more preferably greater than 90%, more preferably greater than 95% or, in another embodiment, has 98 to 100% sequence identity with SEQ ID NO:2, SEQ ID NO:4, SEQ ID NO:6, SEQ ID NO:8, SEQ ID NO:10, SEQ ID NO:12, or SEQ ID NO:14.

In a particularly preferred embodiment, a fragment of the HsMCAK protein comprising a portion of its hydrolytically active "motor" domain is used. This motor domain has been cloned and expressed in bacteria such that large quantities of biochemically active, substantially pure protein are available. Preferably, the target protein comprises an amino acid sequence which has greater than 70% sequence identity with SEQ ID NO:2, SEQ ID NO:4, SEQ ID NO:6, SEQ ID NO:8, SEQ ID NO:10, SEQ ID NO:12, or SEQ ID NO:14, preferably greater than 80%, more preferably greater than 90%, more preferably greater than 95% or, in another embodiment, has 98 to 100% sequence identity with SEQ ID NO:2, SEQ ID NO:4, SEQ ID NO:6, SEQ ID NO:8, SEQ ID NO:10, SEQ ID NO:12, or SEQ ID NO:14.

A particularly preferred embodiment is drawn to a fragment of the HsMCAK protein SEQ ID NO:2, SEQ ID NO:4, SEQ ID NO:6, SEQ ID NO:8, SEQ ID NO:10, SEQ ID NO:12, or SEQ ID NO:14. More preferably, this fragment is tagged at the C-terminus with a myc epitope and 6 histidines. More preferably, this fragment is tagged at the N-terminus with a T7 epitope and at the C-terminus with a myc epitope and 6 histidines.

In one aspect, the nucleic acids provided herein are defined by the proteins encoded thereby. A preferred embodiment of the invention is drawn to an isolated nucleic acid sequence encoding a microtubule motor protein, wherein the motor protein has the following properties: (i) the protein's activity includes microtubule stimulated ATPase activity; and (ii) the protein has a sequence that has greater than 70% sequence identity with SEQ ID NO:2, SEQ ID NO:4, SEQ ID NO:6, SEQ ID NO:8, SEQ ID NO:10, SEQ ID NO:12, or SEQ ID NO:14, preferably greater than 80%, more preferably greater than 90%, more preferably greater than 95% or, in another embodiment, has 98 to 100% sequence identity with SEQ ID NO:2, SEQ ID NO:4, SEQ ID NO:6, SEQ ID NO:8, SEQ ID NO:10, SEQ ID NO:12, or SEQ ID NO:14. In one embodiment, the nucleic acid encodes HsMCAK or a fragment thereof. In another embodiment, the nucleic acid encodes SEQ ID NO:2, SEQ ID NO:4, SEQ ID NO:6, SEQ ID NO:8, SEQ ID NO:10, SEQ ID NO:12, or SEQ ID NO:14.

In one embodiment, the nucleic acid comprises a sequence which has one or more of the following characteristics: greater than 55 or 60% sequence identity with SEQ ID NO:1, SEQ ID NO:3, SEQ ID NO:5, SEQ ID NO:7, SEQ ID NO:8, SEQ ID NO:10, SEQ ID NO:11, or SEQ ID NO:13, preferably greater than 70%, more preferably greater than 80%, more preferably greater than 90 or 95% or, in another embodiment, has 98 to 100% sequence identity with SEQ ID NO:1, SEQ ID NO:3, SEQ ID NO:5, SEQ ID NO:7, SEQ ID NO:8, SEQ ID NO:10, SEQ ID NO:11, or SEQ ID NO:13. In another embodiment provided herein, the nucleic acid hybridizes under stringent conditions to a nucleic acid having a sequence or complementary sequence of SEQ ID NO: 1, SEQ ID NO:3, SEQ ID NO:5, SEQ ID NO:7, SEQ ID NO:8, SEQ ID NO:10, SEQ ID NO:11, or SEQ ID NO:13. In another embodiment, the nucleic acid has a nucleotide sequence of SEQ ID NO:1, SEQ ID NO:3, SEQ ID NO:5, SEQ ID NO:7, SEQ ID NO:8, SEQ ID NO:10, SEQ ID NO:11, or SEQ ID NO:13. As described above, when describing the nucleotide in terms of SEQ ID NO:1, SEQ ID NO:3, SEQ ID NO:5, SEQ ID NO:7, SEQ ID NO:8, SEQ ID NO:10, SEQ ID NO:11, or SEQ ID NO:13, the sequence identity may be slightly lower due to the degeneracy in the genetic code.

As will be appreciated by those in the art, the target proteins can be made in a variety of ways, including both synthesis de novo and by expressing a nucleic acid encoding the protein.

Numerous suitable methods for recombinant protein expression, including generation of expression vectors, generation of fusion proteins, introducing expression vectors into host cells, protein expression in host cells, and purifications methods are known to those in the art.

In a preferred embodiment, the target proteins are purified for use in the assays to provide substantially pure samples. Alternatively, the target protein need not be substantially pure as long as the sample comprising the target protein is substantially free of other components that can contribute to the production of ADP or phosphate.

The target proteins may be isolated or purified in a variety of ways known to those skilled in the art depending on what other components are present in the sample. Standard purification methods include electrophoretic, molecular, immunological, and chromatographic techniques, including ion exchange, hydrophobic, affinity, and reverse-phase HPLC chromatography, and chromatofocussing. For example, the target protein can be purified using a standard anti-target antibody column. Ultrafiltration and diafiltration techniques, in conjunction with protein concentration, are also useful. Either naturally occurring or recombinant target protein can be purified for use in functional assays. The target protein may be purified to substantial purity by standard techniques, including selective precipitation with such substances as ammonium sulfate; column chromatography, immunopurification methods, and others (see, e.g., Scopes, Protein Purification: Principles and Practice (1982); U.S. Pat. No. 4,673,641; Ausubel et al. supra; and Sambrook et al., supra). A preferred method of purification is use of Ni-NTA agarose (Qiagen).

Suitable purification schemes for some specific kinesins are outlined in U.S. Ser. No. 09/295,612, filed Apr. 20, 1999, hereby expressly incorporated herein in its entirety for all purposes.

The expressed protein can be purified by standard chromatographic procedures to yield a purified, biochemically active protein. The activity of any of the peptides provided herein can be routinely confirmedy the assays provided herein such as those which assay ATPase activity or microtubule binding activity. Biologically active target protein is useful for identifying modulators of target protein or fragments thereof and kinesin superfamily members using in vitro assays such as microtubule gliding assays, ATPase assays (Kodama et al., J. Biochem. 99:1465–1472 (1986); Stewart et al., Proc. Nat'l Acad. Sci. USA 90:5209–5213 (1993)), and binding assays including microtubule binding assays (Vale et al., Cell 42:39–50 (1985)), as described in detail below.

III. Assays for Modulators of the Target Protein
A. Functional Assays

Assays that can be used to test for modulators of the target protein include a variety of in vitro or in vivo assays, e.g., microtubule gliding assays, binding assays such as microtubule binding assays, microtubule depolymerization assays, and ATPase assays (Kodama et al., J. Biochem. 99: 1465–1472 (1986); Stewart et al., Proc. Nat'l Acad. Sci. USA 90: 5209–5213 (1993); (Lombillo et al., J. Cell Biol. 128:107–115 (1995); (Vale et al., Cell 42:39–50 (1985))).

Modulation is tested by screening for candidate agents capable of modulating the activity of the target protein comprising the steps of combining a candidate agent with the target protein, as above, and determining an alteration in the biological activity of the target protein. Thus, in this embodiment, the candidate agent should both bind to the target protein (although this may not be necessary), and alter its biological or biochemical activity as defined herein. The methods include both in vitro screening methods and in vivo screening of cells for alterations in cell cycle distribution, cell viability, or for the presence, morphology, activity, distribution, or amount of mitotic spindles, as are generally outlined above.

In a preferred embodiment, molecular motor activity is measured by the methods disclosed in Ser. No. 09/314,464, filed May 18, 1999, entitled "Compositions and assay utilizing ADP or phosphate for detecting protein modulators", which is incorporated herein by reference in its entirety. More specifically, this assay detects modulators of any aspect of a kinesin motor function ranging from interaction with microtubules to hydrolysis of ATP. ADP or phosphate is used as the readout for protein activity.

There are a number of enzymatic assays known in the art which use ADP as a substrate. For example, kinase reactions such as pyruvate kinases are known. See, Nature 78:632 (1956) and Mol. Pharmacol. 6:31 (1970). This is a preferred method in that it allows the regeneration of ATP. In one embodiment, the level of activity of the enzymatic reaction is determined directly. In a preferred embodiment, the level of activity of the enzymatic reaction which uses ADP as a substrate is measured indirectly by being coupled to another reaction. For example, in one embodiment, the method further comprises a lactate dehydrogenase reaction under conditions which normally allow the oxidation of NADH, wherein said lactate dehydrogenase reaction is dependent on the pyruvate kinase reaction. Measurement of enzymatic reactions by coupling is known in the art. Furthermore, there are a number of reactions which utilize phosphate. Examples of such reactions include a purine nucleoside phosphorylase reaction. This reaction can be measured directly or indirectly. A particularly preferred embodiments utilizes the pyruvate kinase/lactate dehydrogenase system.

In one embodiment, the detection of the ADP or phosphate proceeds non-enzymatically, for example, by binding or reacting the ADP or phosphate with a detectable compound.

For example, phosphomolybdate based assays may be used which involve conversion of free phosphate to a phosphomolybdate complex. One method of quantifying the phosphomolybdate is with malachite green. Alternatively, a fluorescently labeled form of a phosphate binding protein, such as the $E. coli$ phosphate binding protein, can be used to measure phosphate by a shift in its fluorescence.

In addition, target protein activity can be examined by determining modulation of target protein in vitro using cultured cells. The cells are treated with a candidate agent and the effect of such agent on the cells is then determined either directly or by examining relevant surrogate markers. For example, characteristics such as mitotic spindle morphology and cell cycle distribution can be used to determine the effect.

Thus, in a preferred embodiment, the methods comprise combining a target protein and a candidate agent, and determining the effect of the candidate agent on the target protein. Generally a plurality of assay mixtures are run in parallel with different agent concentrations to obtain a differential response to the various concentrations. Typically, one of these concentrations serves as a negative control, i.e., at zero concentration or below the level of detection.

As will be appreciated by those in the art, the components may be added in buffers and reagents to assay target protein activity and give optimal signals. Since the methods allow kinetic measurements, the incubation periods can be optimized to give adequate detection signals over the background.

In a preferred embodiment, an antifoam or a surfactant is included in the assay mixture. Suitable antifoams include, but are not limited to, antifoam 289 (Sigma). Suitable surfactants include, but are not limited to, Tween, Tritons, including Triton X- 100, saponins, and polyoxyethylene ethers. Generally, the antifoams, detergents, or surfactants are added at a range from about 0.01 ppm to about 10 ppm.

A preferred assay design.is also provided. In one aspect, the invention provides a multi-time-point (kinetic) assay, with at least two data points being preferred. In the case of multiple measurements, the absolute rate of the protein activity can be determined.

B. Binding Assays

In a preferred embodiment, the binding of the candidate agent is determined through the use of competitive binding assays. In this embodiment, the competitor is a binding moiety known to bind to the target protein, such as an antibody, peptide, binding partner, ligand, etc. Under certain circumstances, there may be competitive binding as between the candidate agent and the binding moiety, with the binding moiety displacing the candidate agent.

Competitive screening assays may be done by combining the target protein and a drug candidate in a first sample. A second sample comprises a candidate agent, the target protein and a compound that is known to modulate the target protein. This may be performed in either the presence or absence of microtubules. The binding of the candidate agent is determined for both samples, and a change, or difference in binding between the two samples indicates the presence of an agent capable of binding to the target protein and potentially modulating its activity. That is, if the binding of the candidate agent is different in the second sample relative to the first sample, the candidate agent is capable of binding to the target protein.

In one embodiment, the candidate agent is labeled. Either the candidate agent, or the competitor, or both, is added first to the target protein for a time sufficient to allow binding. Incubations may be performed at any temperature which facilitates optimal activity, typically between 4 and 40° C. Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate agent. Displacement of the competitor is an indication the candidate agent is binding to the target protein and thus is capable of binding to, and potentially modulating, the activity of the target protein. In this embodiment, either component can be labeled. Thus, for example, if the competitor is labeled, the presence of label in the wash solution indicates displacement by the agent.

Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to the target protein with a higher affinity. Thus, if the candidate agent is labeled, the presence of the label on the support, coupled with a lack of competitor binding, may indicate the candidate agent is capable of binding to the target protein.

C. Candidate Agents

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. In a preferred embodiment, the candidate agents are organic chemical moieties, a wide variety of which are available in the literature.

D. Other Assay Components

The assays provided utilize target protein as defined herein. In one embodiment, portions of target protein are utilized; in a preferred embodiment, portions having target protein activity as described herein are used. In addition, the assays described herein may utilize either isolated target proteins or cells or animal models comprising the target proteins.

A variety of other reagents may be included in the screening assays. These include reagents like salts, neutral proteins, e.g. albumin, detergents, etc which may be used to facilitate optimal protein-protein binding and/or reduce non-specific or background interactions. Also, reagents that otherwise improve the efficiency of the assay, such as protease inhibitors, nuclease inhibitors, anti-microbial agents, etc., may be used. The mixture of components may be added in any order that provides for the requisite binding.

IV. Applications

The methods of the invention are used to identify compounds useful in the treatment of cellular proliferation diseases. Disease states which can be treated by the methods and compositions provided herein include, but are not limited to, cancer (further discussed below), autoininune disease, arthritis, graft rejection, inflammatory bowel disease, proliferation induced after medical procedures, including, but not limited to, surgery, angioplasty, and the like. It is appreciated that in some cases the cells may not be in a hyper or hypo proliferation state (abnormal state) and still require treatment. For example, during wound healing, the cells may be proliferating "normally", but proliferation enhancement may be desired. Similarly, as discussed above, in the agriculture arena, cells may be in a "normal" state, but proliferation modulation may be desired to enhance a crop by directly enhancing growth of a crop, or by inhibiting the growth of a plant ororganism which adversely affects the crop. Thus, in one embodiment, the invention herein includes application to cells or individuals afflicted or impending affliction with any one of these disorders or states.

The compositions and methods provided herein are particularly deemed useful for the treatment of cancer including solid tumors such as skin, breast, brain, cervical carcinomas, testicular carcinomas, etc. More particularly, cancers that may be treated by the compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated larae cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinorna, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinorna, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squarnous cell carcinoma, botryoid sarcoma (embryonal rhabdomyosarcoma], fallopian tubes (carcinoma); Hematoloeic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal Qlands: neuroblastoma. Thus, the term "cancerous cell" as provided herein, includes a cell afflicted by any one of the above identified conditions.

Accordingly, the compositions of the invention are administered to cells. By "administered" herein is meant administration of a therapeutically effective dose of the candidate agents of the invention to a cell either in cell culture or in a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art. By "cells" herein is meant almost any cell in which mitosis or meiosis can be altered.

A "patient" for the purposes of the present invention includes both humans and other animals, particularly mammals, arid other organisms. Thus the methods are applicable to both human therapy and veterinary applications. In the preferred embodiment the patient is a mammal, and in the most preferred embodiment the patient is human.

Candidate agents having the desired pharmacological activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1–100 wt.%. The agents maybe administered alone or in combination with other treatments, i.e., radiation, or other chemotherapeutic agents.

In a preferred embodiment, the pharmaceutical compositions are in a water soluble form, such as pharmaceutically acceptable salts, which is meant to include both acid and base addition salts.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents. The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations. The administration of the candidate agents of the present invention can be done in a variety of ways as discussed above, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the candidate agents may be directly applied as a solution or spray.

One of skill in the art will readily appreciate that the methods described herein also can be used for diagnostic applications. A diagnostic as used herein is a compound or method that assists in the identification and characterization of a health or disease state in humans or other animals.

The present invention also provides for kits for screening for modulators of the target protein. Such kits can be prepared from readily available materials and reagents. For example, such kits can comprise any one or more of the following materials: biologically active target protein, reaction tubes, and instructions for testing activity of the target protein. Preferably, the kit contains biologically active target protein. A wide variety of kits and components can be prepared according to the present invention, depending upon the intended user of the kit and the particular needs of the user. For example, the kit can be tailored for ATPase assays, microtubule gliding assays, or microtubule binding assays.

V. Examples

This assay is based on detection of ADP production from a target protein's microtubule stimulated ATPase. ATP production is monitored by a coupled enzyme system consisting of pyruvate kinase and lactate dehydrogenase. Under the assay conditions described below, pyruvate kianse catalyzes the conversion of ADP and phosphoenol pyruvate to pyruvate and ATP. Lactate dehydrogenase then catalyzes the oxidation-reduction reaction of pyruvate and NADH to lactate and AND+. Thus, for each molecule of ADP produced, one molecule of NADH is consumed. The amount of NADH in the assay solution is monitored by measuring light absorbance at a wavelength of 340 nm.

The final 25 $\mu$l assay solution consists of the following: 5 $\mu$g/ml target protein, 30 $\mu$g/ml microtubules, 5 $\mu$M Taxol, 0.8 mM NADH, 1.5 mM phosphoenol pyruvate, 3.5 U/ml pyruvate kinase, 5 U/ml lactate dehydrogenase, 25 mM Pipes/KOH pH 6.8, 2 mM $MgCl_2$, 1 mM EGTA, 1 mM MDTT, 0.1 mg/ml BSA, 0.001% antifoam 289, and 1 mM ATP.

Potential candidate agents are dissolved in DMSO at a concentration of about 1 mg/ml and 0.5 $\mu$l of each chemical solution is dispensed into a single well of a clear 384 well plate. Each of the 384 wells are then filled with 20 $\mu$l of a solution consisting of all of the assay components described above except for ATP. The plate is agitated at a high frequency. To start the assay, 5 $\mu$l of a solution containing ATP is added to each well. The plate is agitated and the absorbance is read at 340 nm over various time intervals. The assay is run at room temperature.

The assay components and the performance of the assay are optimized together to match the overall read time with the rate of the target protein's ADP production. The read time should be long enough for the rate of NADH consumption to reach steady state beyond an initial lag time of several seconds.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety.

What is claimed is:

1. An isolated nucleic acid sequence, wherein the nucleic acid encodes a motor protein comprising SEQ ID NO:2, SEQ ID NO:4, SEQ ID NO:6, SEQ ID NO:8; SEQ ID NO:10, SEQ ID NO:12 or SEQ ID NO:14 that has microtubule-stimulated ATPase activity.

2. The isolated nucleic acid sequence of claim 1, wherein the nucleic acid has a nucleotide sequence of SEQ ID NO:1, SEQ ID NO:3, SEQ ID NO:5, SEQ ID NO:7, SEQ ID NO:9, SEQ ID NO:11, or SEQ ID NO:13.

3. The nucleic acid of claim 1, further comprising a promoter sequence operably linked to the isolated nucleic acid sequence.

4. The nucleic acid of claim 3, wherein the promoter is a constitutive promoter.

5. The nucleic acid of claim 3, wherein the promoter is an inducible promoter.

6. The nucleic acid of claim 2, further comprising a promoter sequence operably linked to the isolated nucleic acid sequence.

7. The nucleic acid of claim 6, wherein the promoter is a constitutive promoter.

8. The nucleic acid of claim 6, wherein the promoter is an inducible promoter.

9. A vector comprising a nucleic acid of claim 1.

10. A vector comprising a nucleic acid of claim 2.

11. A cultured cell comprising the vector of claim 9.

12. A cultured cell comprising the vector of claim 10.

* * * * *

UNITED STATES PATENT AND TRADEMARK OFFICE
CERTIFICATE OF CORRECTION

PATENT NO.    : 6,638,754 B1
DATED         : October 28, 2003
INVENTOR(S)   : Christophe Beraud and Roman Sakowicz It is certified that error appears in the above-identified patent and that said Letters Patent is hereby corrected as shown below:

<u>Title page,</u>
Item [75], Inventors, "Christophe Beraud, San Francisco, CA" should read
-- Christophe Beraud, Palm Springs, CA --

Signed and Sealed this

Ninth Day of March, 2004

JON W. DUDAS
*Acting Director of the United States Patent and Trademark Office*